US009480835B2

(12) United States Patent
Jang et al.

(10) Patent No.: US 9,480,835 B2
(45) Date of Patent: Nov. 1, 2016

(54) ASSEMBLY OF PASSIVE CARDIAC ELECTRICAL LEAD

(75) Inventors: Grace Ying Yang Jang, Calabasas, CA (US); Zhijun Cheng, Shanghai (CN); Yongqiang Wei, Shanghai (CN); Jing Wen, Shanghai (CN)

(73) Assignee: SHANGHAI MICROPORT MEDICAL (GROUP) CO., LTD., Shanghai (CN)

( * ) Notice: Subject to any disclaimer, the term of this patent is extended or adjusted under 35 U.S.C. 154(b) by 276 days.

(21) Appl. No.: 14/233,462

(22) PCT Filed: Jun. 28, 2012

(86) PCT No.: PCT/CN2012/077797
§ 371 (c)(1),
(2), (4) Date: Jan. 17, 2014

(87) PCT Pub. No.: WO2014/000234
PCT Pub. Date: Jan. 3, 2014

(65) Prior Publication Data
US 2014/0123485 A1   May 8, 2014

(51) Int. Cl.
*A61N 1/05*   (2006.01)
*H01R 24/58*   (2011.01)

(52) U.S. Cl.
CPC .............. *A61N 1/05* (2013.01); *A61N 1/056* (2013.01); *H01R 24/58* (2013.01); *H01R 2201/12* (2013.01); *Y10T 29/49117* (2015.01)

(58) Field of Classification Search
CPC .......... A61N 1/04; A61N 1/05; A61N 1/056; H01R 43/00; H01R 43/007; H01R 2201/12; H01R 24/58; Y10T 29/49117
See application file for complete search history.

(56) References Cited

U.S. PATENT DOCUMENTS

| | | | | |
|---|---|---|---|---|
| 4,437,474 A | * | 3/1984 | Peers-Trevarton | .... A61N 1/056 29/605 |
| 4,922,607 A | | 5/1990 | Doan et al. | |

(Continued)

FOREIGN PATENT DOCUMENTS

| | | |
|---|---|---|
| CN | 201329130 Y | 10/2009 |
| EP | 1847290 A1 | 10/2007 |

(Continued)

OTHER PUBLICATIONS

International Search Report and Written Opinion in connection with International Patent Application No. PCT/CN20121077783 filed Jun. 28, 2012. Apr. 4, 2013 (13 pages).

(Continued)

*Primary Examiner* — Carl Arbes
(74) *Attorney, Agent, or Firm* — Kilpatrick Townsend & Stockton LLP

(57) ABSTRACT

A passive cardiac electrical lead is assembled by coupling an inner conductor coil to a connector pin to form an inner conductor assembly. The inner conductor assembly is threaded through a connector insulator. An insulator tubing is placed over the inner coil. A proximal end of the insulator tubing is sleeved over the distal extension of the connector insulator. An outer conductor coil is coupled to a ring connector to form an outer conductor assembly. The inner conductor assembly is threaded through the outer conductor assembly. The ring connector is sleeved on the distal extension of the connector insulator and over the insulator tubing. A proximal seal is sleeved over a socket end of the connector pin. A portion of the proximal seal is seated on the proximal extension of the connector insulator.

20 Claims, 25 Drawing Sheets

(56) References Cited

U.S. PATENT DOCUMENTS

| | | | | |
|---|---|---|---|---|
| 4,944,088 | A | * | 7/1990 | Doan ................ A61N 1/056 29/858 |
| 5,231,996 | A | * | 8/1993 | Bardy ................ A61N 1/056 606/108 |
| 5,417,208 | A | * | 5/1995 | Winkler ............. A61N 1/056 607/122 |
| 5,514,172 | A | | 5/1996 | Mueller |
| 5,741,321 | A | | 4/1998 | Brennen |
| 6,052,625 | A | | 4/2000 | Marshall |
| 6,183,305 | B1 | | 2/2001 | Doan et al. |
| 6,801,809 | B2 | * | 10/2004 | Laske ................ A61N 1/056 607/122 |
| 7,383,091 | B1 | | 6/2008 | Chitre et al. |
| 7,715,926 | B2 | * | 5/2010 | Boser ................ A61N 1/04 439/394 |
| 2011/0220408 | A1 | | 9/2011 | Walsh et al. |
| 2012/0157810 | A1 | | 6/2012 | Doerr et al. |

FOREIGN PATENT DOCUMENTS

| | | |
|---|---|---|
| WO | 2004/011081 A1 | 2/2004 |
| WO | 2007/073435 A1 | 6/2007 |
| WO | 2008/153451 A1 | 12/2008 |
| WO | 2009/078752 A1 | 6/2009 |
| WO | 2010/112245 A1 | 10/2010 |
| WO | 2012/058547 A1 | 5/2012 |

OTHER PUBLICATIONS

International Search Report and Written Opinion in connection with International Patent Application No. PCT/CN2012/077797 filed Jun. 28, 2012. Apr. 4, 2013 (11 pages).

International Search Report and Written Opinion in connection with International Patent Application No. PCT/CN2012/077806 filed Jun. 28, 2012. Apr. 4, 2013 (10 pages).

International Search Report and Written Opinion in connection with International Patent Application No. PCT/CN2011/081808 filed Nov. 4, 2011. Aug. 16, 2012 (11 pages).

International Search Report and Written Opinion in connection with International Patent Application No. PCT/CN2011/081799 filed Nov. 4, 2011. Aug. 16, 2012 (10 pages).

International Search Report and Written Opinion in connection with International Patent Application No. PCT/CN2011/081805 filed Nov. 4, 2011. Aug. 9, 2012 (10 pages).

* cited by examiner

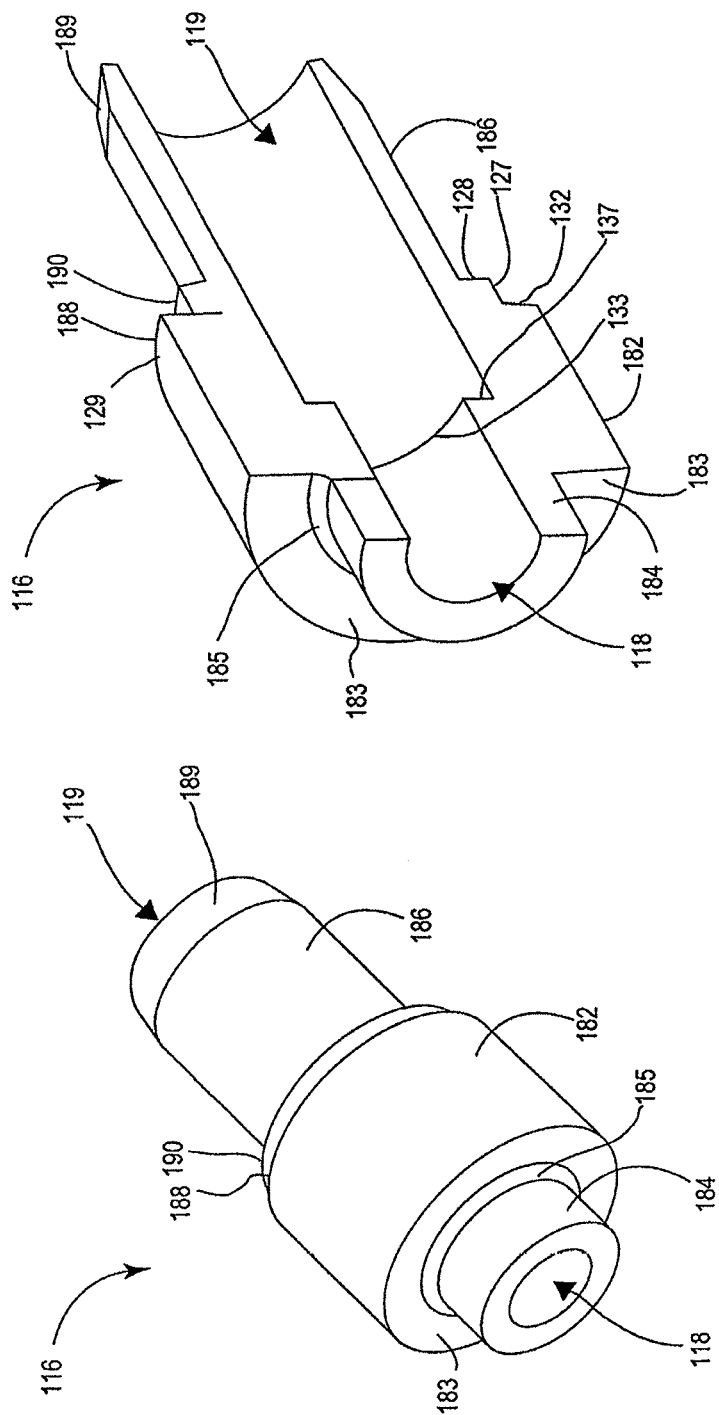

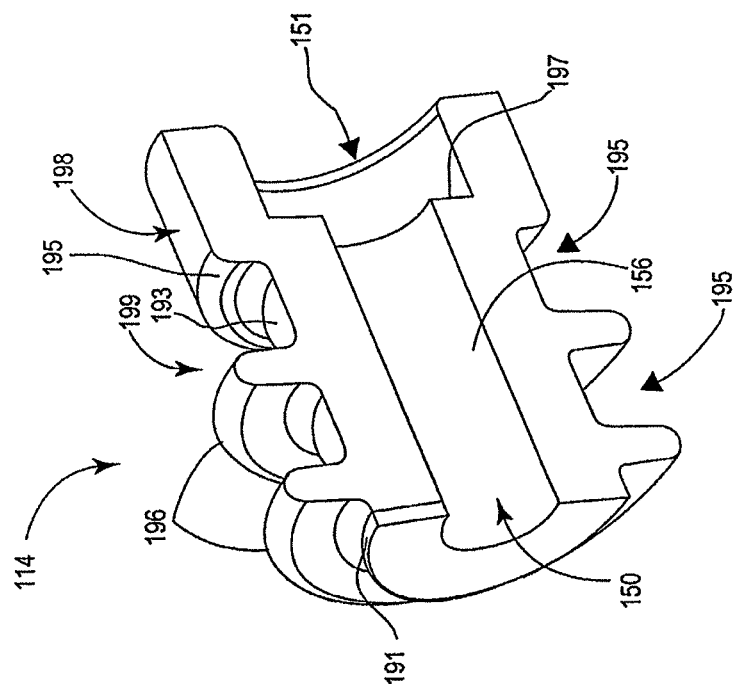
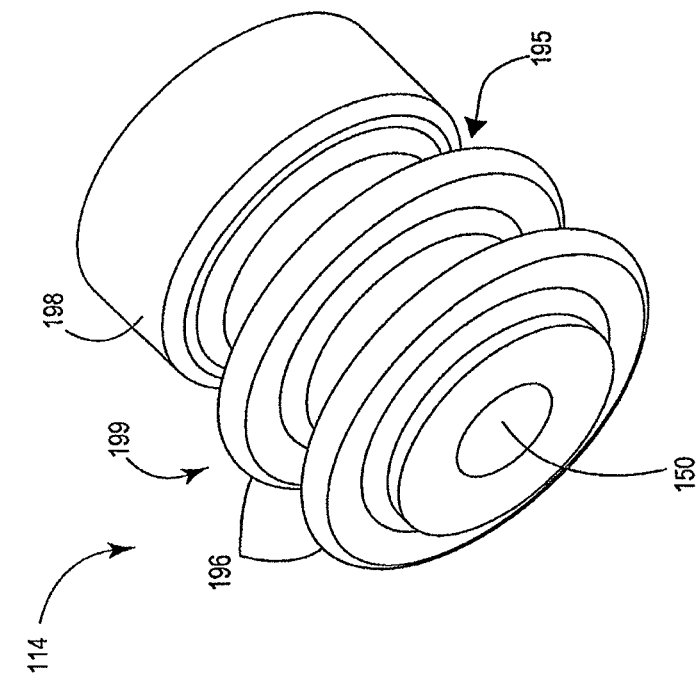

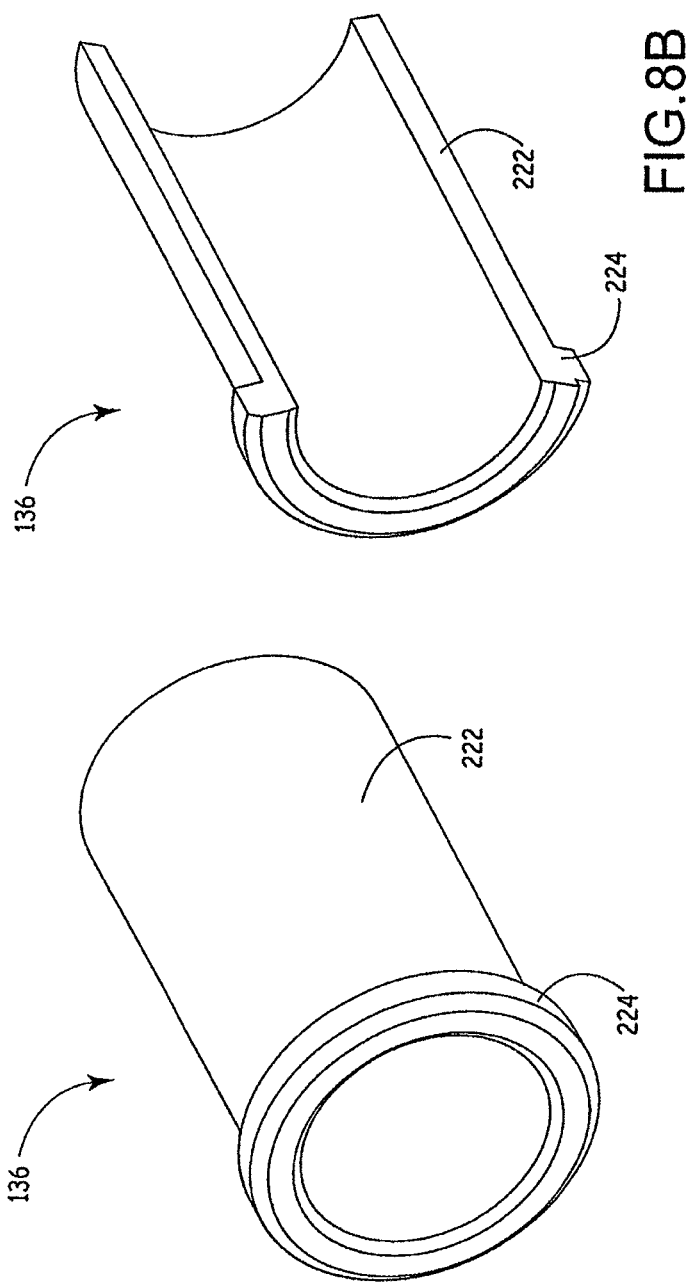

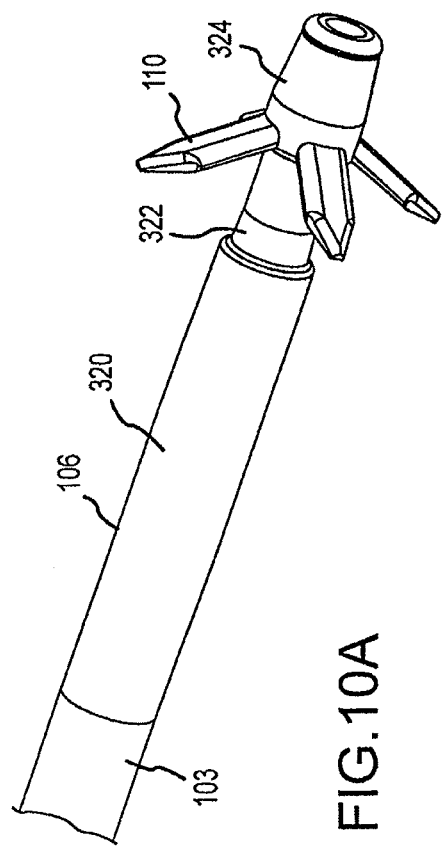
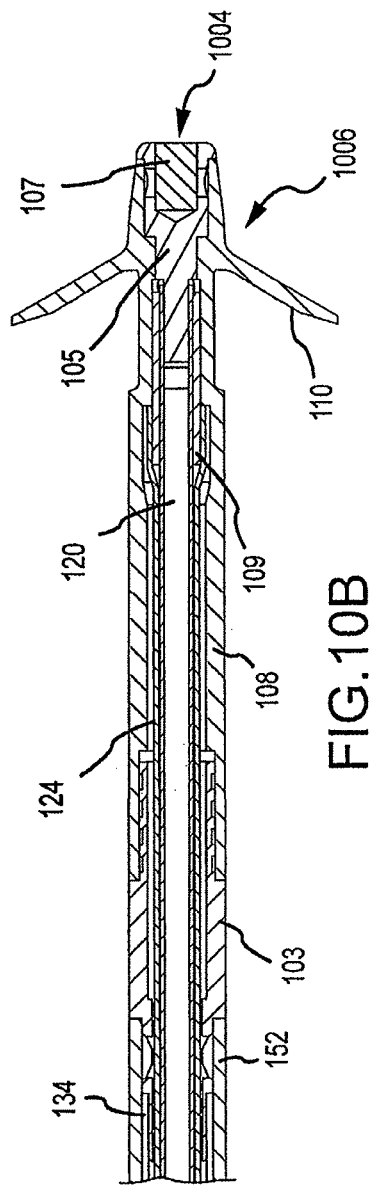
FIG.10A
FIG.10B

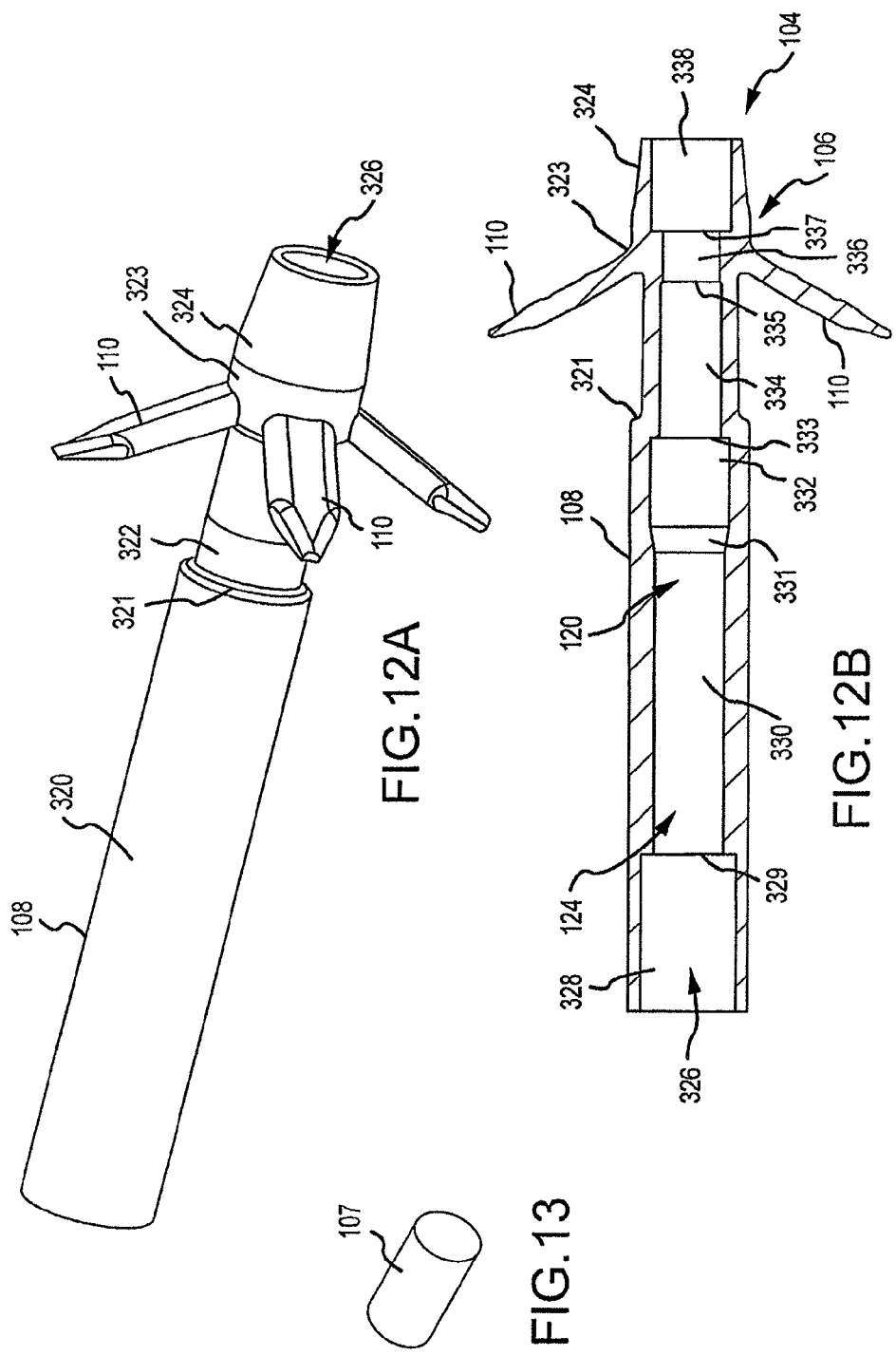

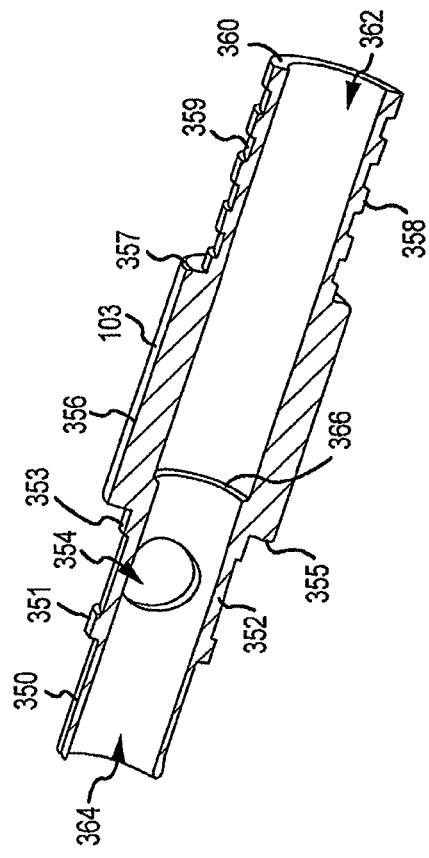
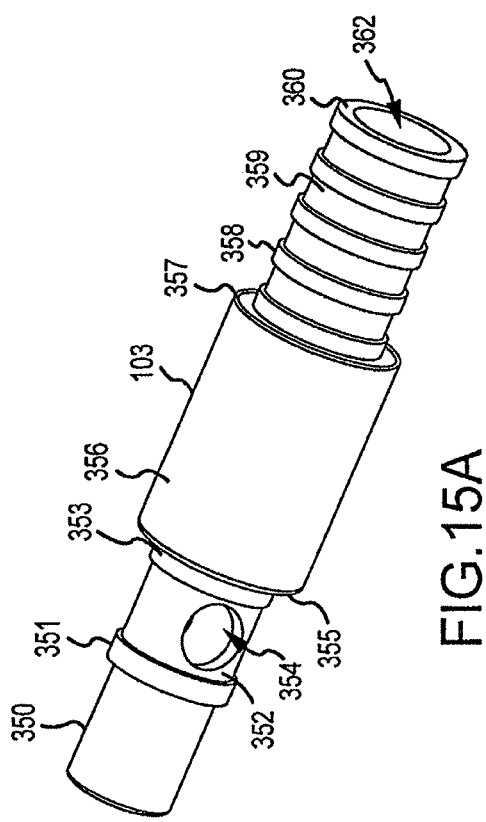
FIG. 15B
FIG. 15A

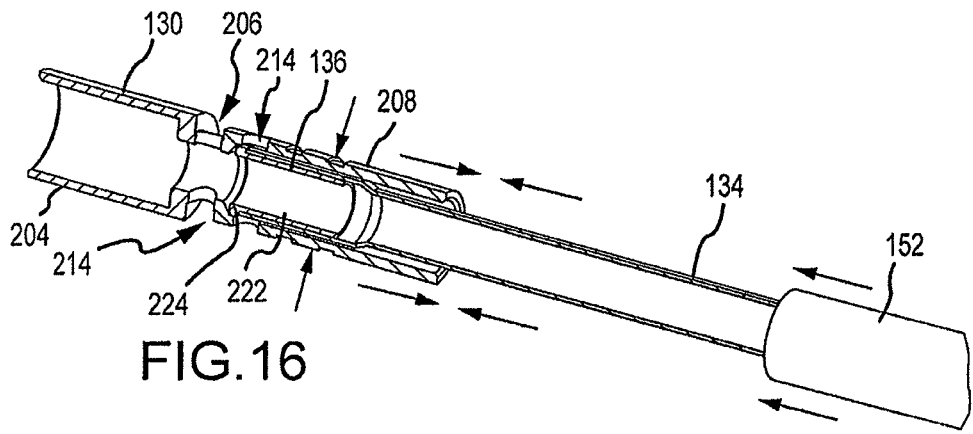
FIG.16
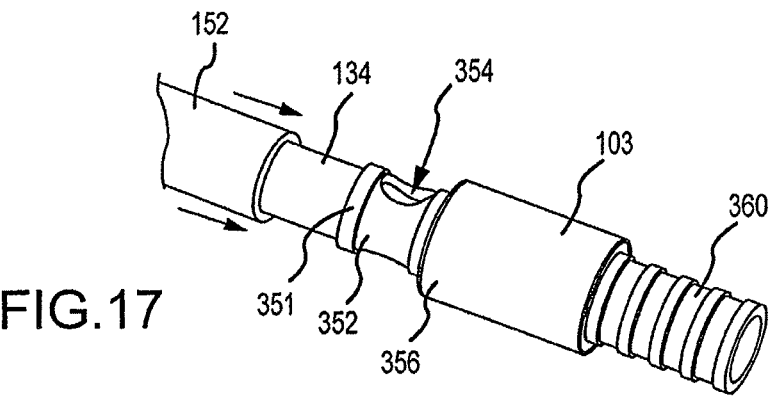
FIG.17
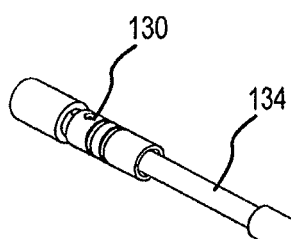
FIG.18
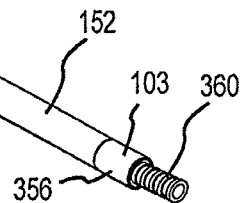

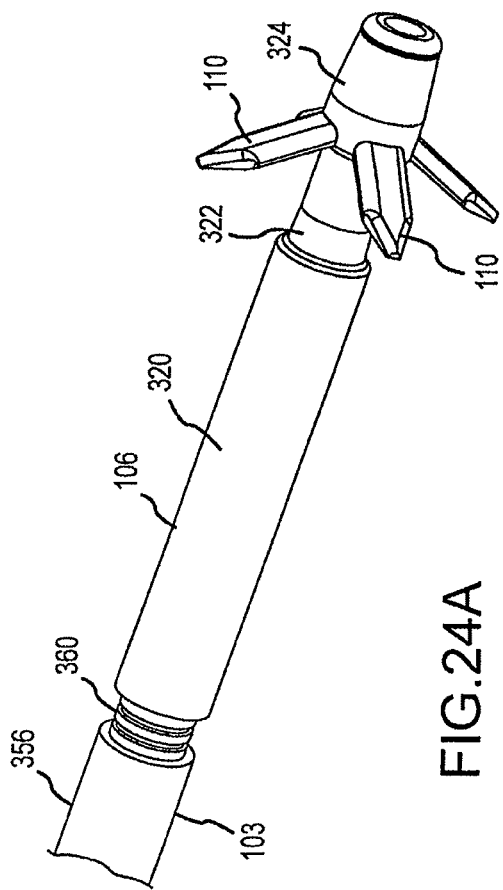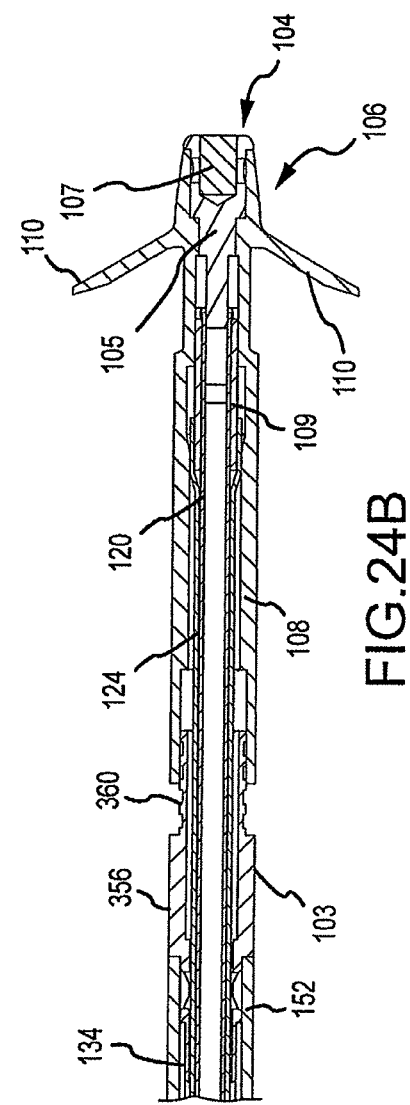
FIG. 24A
FIG. 24B

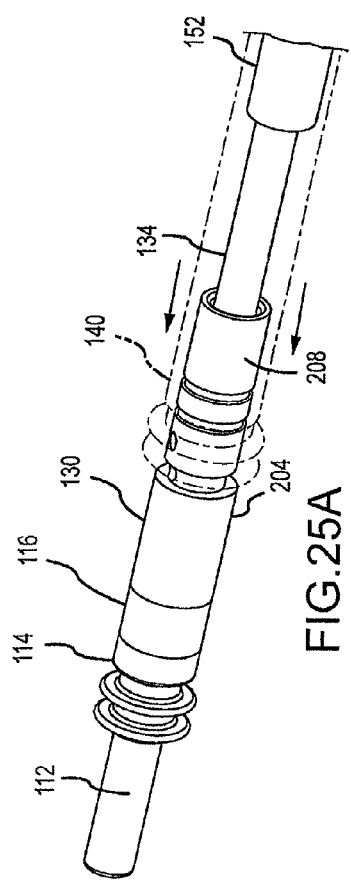
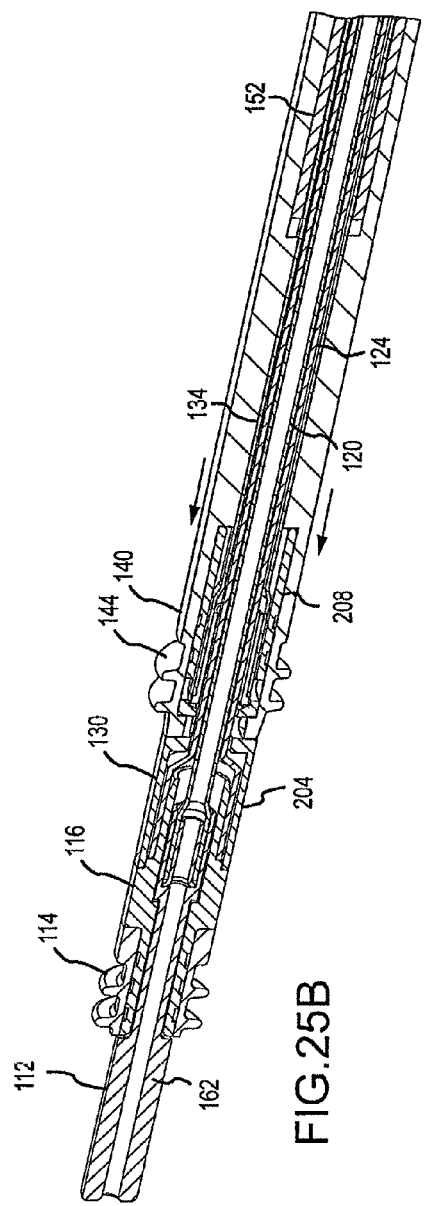
FIG.25A
FIG.25B

ASSEMBLY OF PASSIVE CARDIAC ELECTRICAL LEAD

This application is a 35 USC 371 national stage of PCT Patent Application No. PCT/CN2012/077797, filed Jun. 28, 2012, entitled "Assembly of Passive Cardiac Electrical Lead," the entire contents of which is hereby incorporated by reference herein, in its entirety.

TECHNICAL FIELD

The present disclosure relates generally to implantable electrical leads. More particularly, the present disclosure relates to connection end features of implantable electrical leads where the lead is connected to an associated defibrillator, pacemaker, or other electrical stimulation device. Still more particularly, the present disclosure relates to methods for assembly of implantable electrical leads having a passive mechanism on a treatment end thereof.

BACKGROUND

Electrodes are often used to stimulate contraction of the heart. For example, when a patient's heart is functioning with an abnormal rhythm, electrical energy may be applied to the heart via the electrodes to return the heart to a normal rhythm. In some cases this procedure may be an isolated event while in other cases a more frequent, regular, or even continuous process is used. In these cases electrodes may be incorporated into a lead that is used with a pacemaker, defibrillator, or other electrical stimulation device such that pacing pulses may be delivered, for example, to an atrium or ventricle of a heart. The system including the electrical stimulation device and the lead may be implantable and, thus, used over long periods of time.

In general, a lead includes a pair of electrodes disposed at a distal end of the lead which may be positioned in the right ventricle or the right atrium of the heart. The proximal end of the lead may be coupled to a defibrillator or a pacemaker and conductors may deliver electrical impulses along the length of the lead to the electrode thereby delivering pacing pulses to the heart.

There are at least two conventional types of leads. The first type of leads is referred to as an active electrical lead with an active mechanism at the distal end. The second type of leads is referred to as a passive electrical lead with a passive mechanism at the distal end.

The distal end of a typical active electrical lead may include a helix type fixation mechanism designed to be actuated and axially extend and/or rotate out of a tip portion of the lead to engage or embed into the endocardium. The distal end of a typical passive electrical lead may include an anchor type fixation mechanism designed to anchor the distal end in the heart. The fixation mechanism for a passive lead, for example, may include one or more radially spaced tines that secure the distal end in the heart.

The proximal end of pacemaker and defibrillator leads are commonly designed and manufactured to a standard such as China Standard YY/T 0491-2004//ISO 5841-3, 2000. The standard is applicable to both active and passive pacemaker or defibrillator leads. Within that standard, medical device implant companies commonly have their own unique designs. Among the technologies used to meet the standard, are laser welding and metal crimping resulting in highly reliable pacemaker and defibrillator lead joint connections.

The design of defibrillator and pacemaker leads has evolved over time. Over time and at present, the proximal end of an active electrical lead and the proximal end of a passive electrical lead are generally designed differently due to their functional differences. That is, the proximal end of an active lead may be designed to actuate and/or control the distal active mechanism, while the proximal end of a passive lead may not include such actuation and/or control features. System designs and assembly processes of the passive and active electrical leads are, thus, different. As a result, the overall cost of having significant different system designs and assembly processes is relatively high and a system having common features or similar or exchangeable components between an active electrical lead and a passive electrical lead may be less expensive and more attractive to consumers.

The information included in this Background section of the specification, including any references cited herein and any description or discussion thereof, is included for technical reference purposes only and is not to be regarded subject matter by which the scope of the invention as defined in the claims is to be bound.

SUMMARY

In one embodiment, a method of assembling a passive medical lead is provided. The method may include mechanically and electrically coupling an inner coil to a connector pin to form an inner conductor assembly. The method may also include threading the inner conductor assembly through a connector insulator having a distal extension and a proximal extension. The method may also include arranging an insulator tubing over the inner coil including sleeving a proximal end of the insulator tubing over the distal extension of the connector insulator. The method may further include mechanically and electrically coupling an outer coil to a ring connector to form an outer conductor assembly and threading the inner conductor assembly through the outer conductor assembly. The method may also include sleevably arranging the ring connector on the distal extension of the connector insulator and over the insulator tubing. The method may also include sleeving a proximal seal over a socket end of the connector pin, arranging a flushing portion of the proximal seal on the proximal extension of the connector insulator and seating a sealing portion of the proximal seal on a bar portion of the connector pin between the socket end of the connector pin and the proximal extension of the connector insulator. The method may also include adhering the sealing portion of the proximal seal to the bar portion of the connector pin.

In another exemplary implementation, a method of assembling a passive medical lead may include initially assembling an inner conductor assembly including a flexible inner conductor of a first diameter and an insulating covering over the flexible inner conductor. An outer conductor assembly may be assembled including a tubular flexible outer conductor of a second diameter larger than the first diameter and a thickness of the insulating covering. The inner conductor assembly may be threaded through the outer conductor assembly.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter. A more extensive presentation of features, details, utilities, and advantages of the present invention is provided in the following written description of various embodiments of the invention, illustrated in the accompanying drawings, and defined in the appended claims.

BRIEF DESCRIPTION OF THE FIGURES

FIGS. 5A and 5B are an isometric view and an isometric cross-sectional view, respectively, of a connector insulator of the lead of FIGS. 1 and 2.

FIGS. 6A and 6B are an isometric view and an isometric cross-sectional view, respectively, of a proximal seal of the lead of FIGS. 1 and 2.

FIGS. 8A and 8B are an isometric view and an isometric cross-sectional view, respectively, of a ring sleeve of the lead of FIGS. 1 and 2.

FIGS. 10A and 10B are an isometric view and an isometric cross-sectional view, respectively, of a distal end of the lead of FIG. 1.

FIGS. 12A and 12B are an isometric view and an isometric cross-sectional view, respectively, of a passive tip sheath of the lead of FIGS. 1, 10A, and 10B.

FIG. 13 is an isometric view of a steroid insert for the passive tip sheath of the lead of FIGS. 1, 10A, and 10B.

FIGS. 15A and 15B are an isometric view and an isometric cross-sectional view, respectively, of a ring electrode of the lead of FIGS. 1, 10A, and 10B.

FIG. 16 is a cross-section view of the ring connector in the process of being crimped to the outer coil conductor in an exemplary method of assembly of an exemplary passive cardiac electrical lead.

FIG. 17 is an isometric view of the ring electrode in the process of being attached and welded to the distal end of the outer coil conductor in an exemplary method of assembly of an exemplary passive cardiac electrical lead.

FIG. 18 is an isometric view of the outer sheath in place on the outer coil conductor between the ring electrode and the ring connector in an exemplary method of assembly of an exemplary passive cardiac electrical lead.

FIG. 24A is an isometric view of the tip electrode being crimped to the distal end of the inner conductor coil in an exemplary method of assembly of an exemplary passive cardiac electrical lead.

FIG. 24B is a cross-sectional view of FIG. 24A with the addition of the steroid in the tip.

FIG. 25A is an isometric view of the passive tip sheath being sleeved over the tip electrode in an exemplary method of assembly of an exemplary passive cardiac electrical lead.

FIG. 25B is a cross-sectional view of FIG. 25A.

DETAILED DESCRIPTION

The present disclosure relates to an implantable electrical lead having a passive mechanism on a distal end (i.e., a passive lead.) The passive lead may include a system of parts on a proximal end thereof that is primarily adapted to connect to and electrically communicate with a defibrillator, pace maker, or other electrical stimulation device. It is noted that some of the parts may be adapted to insulate between other parts and/or between the proximal end and the electrical stimulation device.

Figure 1:
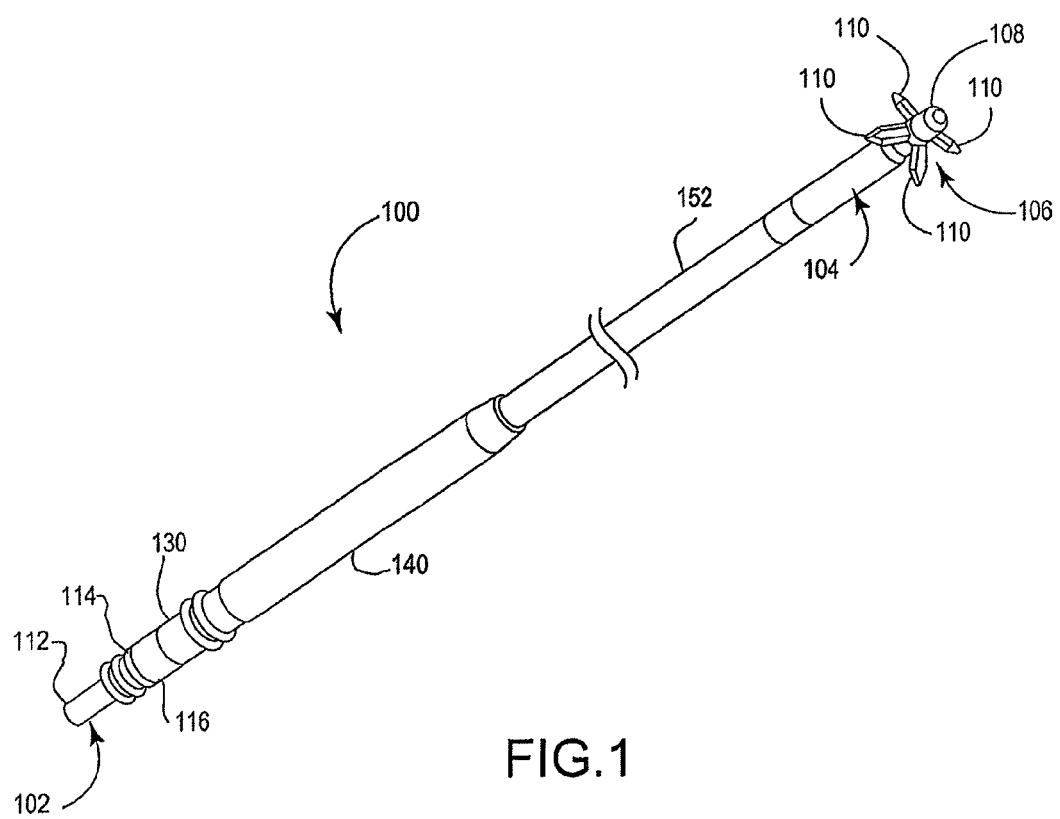
FIG. 1 is an isometric view of an exemplary embodiment of an implantable medical electrical lead with a passive electrode.

FIG. 1 is an isometric view of an embodiment of an implantable medical passive electrical lead 100. The lead 100 has a proximal end 102 and a distal end 104. As shown, a passive tip 106 may be disposed at the distal end 104 and may include passive tip sheath 108 in the form of an anchor-type fixation mechanism. The passive tip sheath 108 may be designed to anchor the lead at a treatment site of a patient such as in the fibrous tissue lining the endocardium of a heart, for example. The passive tip sheath 108 may include one or more radially spaced tines 110 that engage the treatment site or other tissues adjacent to the treatment site thereby holding the distal end at or near the treatment site. As shown in FIG. 1, the lead 100 is longitudinally extended between the distal end 104 and the proximal end 102.

Figure 2:
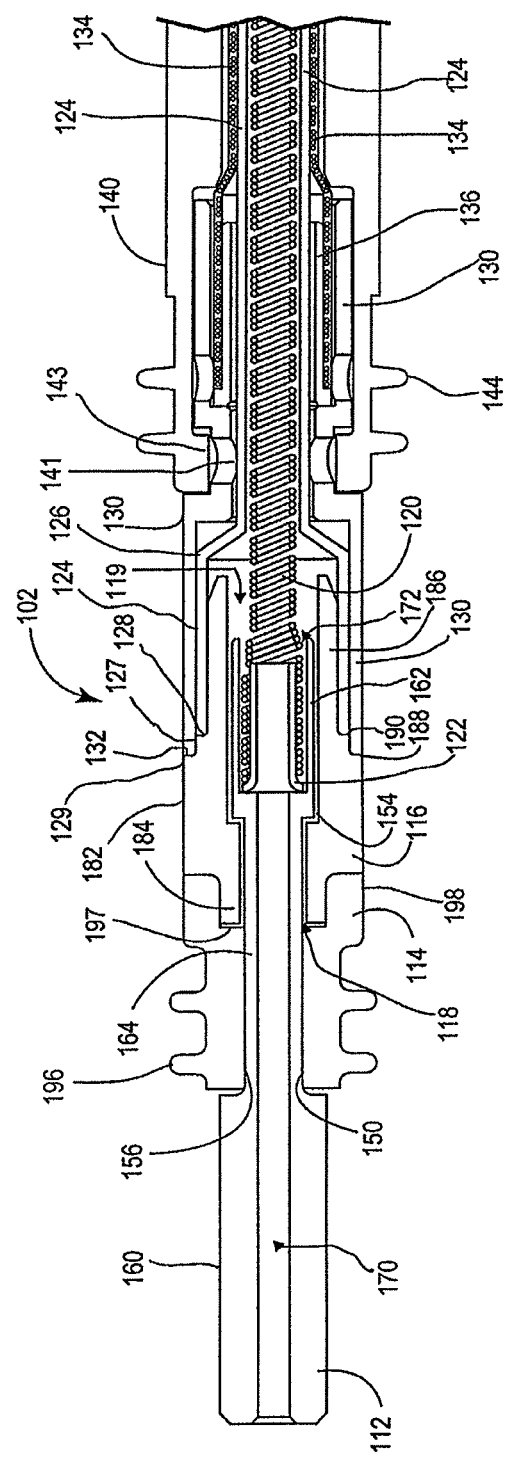
FIG. 2 is a cross-sectional view of a proximal end of the lead of FIG. 1.

Referring now to FIG. 2, the proximal end 102 of the lead 100 includes a system of parts or pieces. The system of parts or pieces may be divided into three categories including inner parts relating to an inner conductor, outer parts relating to an outer conductor, and insulating parts for electrically separating the inner parts from the outer parts. The inner parts may include a conductive connector pin 112, an inner conductor or coil 120, and a pin sleeve 122. The outer parts may include a ring connector 130, an outer conductor or coil 134, and a ring sleeve 136. The inner and outer parts may be substantially separated by the insulating parts including a connector insulator 116 and an insulator tubing 124. A proximal seal 114 and a boot seal 140 may also be provided.

Beginning with the inner parts, the connector pin 112 may be configured for electrical engagement with a defibrillator, pacemaker or other electrical stimulation device and for communicating electrical impulses to the inner conductor or coil 120. As such, the connector pin 112 may be adapted at one end for plugging into a socket of an electrical stimulation device and may be adapted at another end for connecting to the inner conductor or coil 120.

Figure 3:
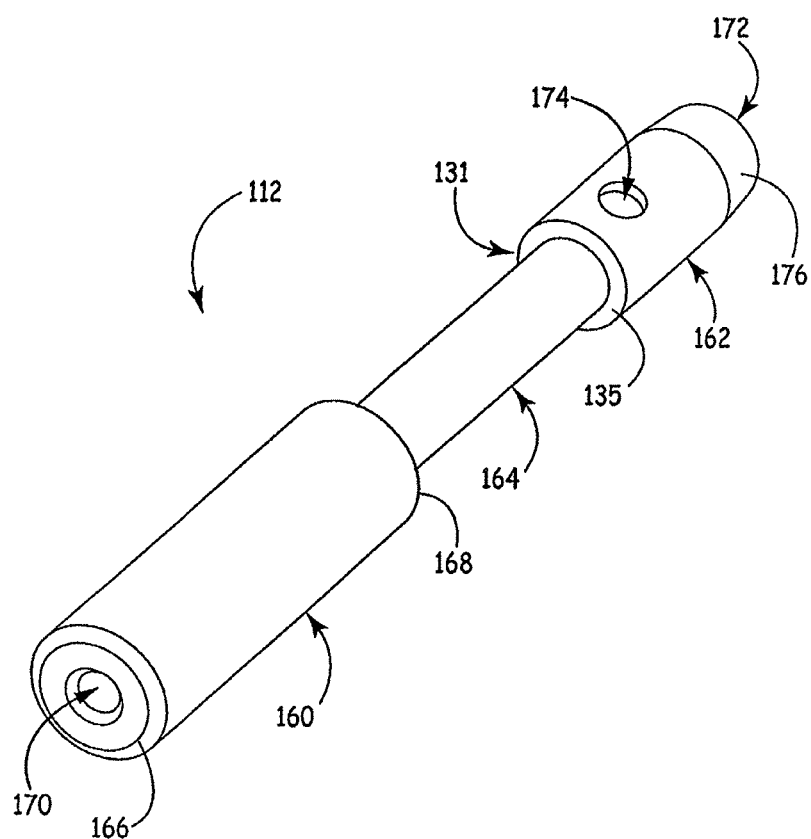
FIG. 3 is an isometric view of a connector pin of the lead of FIGS. 1 and 2.

A close-up view of a connector pin 112 is shown in FIG. 3. As shown, the connector pin 112 may include a socket end 160 and a conductor end 162 and may further include a bar portion 164 extending therebetween. The socket end 160 of the pin 112 may be generally elongate and cylindrically shaped and may have a diameter adapted for placement in a correspondingly shaped socket of an electrical stimulation device. The proximal end of the socket end 160 may include a chamfered edge 166 for guiding the pin 112 into the socket when placing the pin 112 into the electrical device. The distal end of the socket end 160 may include a substantially sharp or square edge 168 for abutting the proximal seal 114 as the case may be.

Exposed portions of the proximal end 102 of the lead 100, like the socket end 160 just described, that may contact or otherwise physically interact with an electrical stimulation device, may be designed to meet industry standard specifications such as the IS-1 specification, for example. As such, while particular parts of the proximal end 102 are described herein as varying in size, diameter, length, or other dimensional variations, in some embodiments, the exposed portions of the parts may be selected to meet such specifications or standards. However, nothing in the present disclosure should be construed to limit the parts to industry standard dimensions.

The bar portion 164 of the connector pin 112 may also be generally elongate and cylindrically shaped and may have a diameter smaller than that of the socket end 160. The bar portion 164 may have a length selected to longitudinally secure the pin 112 relative to the connector insulator 116 and the proximal seal 114. That is, the length of the bar portion 164 may correspond to a bore length in the connector insulator 116 plus a bore length in the proximal seal 114, such that longitudinal motion is substantially prevented relative to the connector insulator 116 and the proximal seal 114. As shown in FIG. 2, the socket end 160 and the bar portion 164 may include a longitudinally extending bore 170 extending from the socket end 160 of the pin 112 to the distal end of the bar portion 164 and exiting into a crimp zone 172 within the conductor end 162 of the pin 112. This bore 170 may be sized and adapted to receive a stylet, for example, when installing or positioning the lead, or when access to the distal end of the lead is desired.

The conductor end 162 of the pin 112 may be substantially cylindrically shaped with an outer diameter slightly larger than that of the bar portion 164 and slightly smaller than that of the socket end 160. Other relationships of diameters of the several portions of the connector pin 112 may also be provided. For example, the conductor end 162 may have an outer diameter larger than the socket end 160. In the exemplary embodiment shown in FIG. 3, the conductor end 162 may be arranged in a relatively congested area where the ring connector 130, the insulator tubing 124, the connector insulator 116, the conductor end 162, the inner conductor 120, and the pin sleeve 122 all overlap. Where the proximal end 102 is designed to meet the IS-1 specification, for example, restrictions on the overall outer diameter together with the congestion may cause the outer diameter of the conductor end 162 to be smaller than the socket end 160.

The conductor end 162 of the pin 112 may include an inner cavity or crimp zone 172 having a substantially cylindrical cross-section with a diameter defining an inner diameter of the conductor end 162. The conductor end 162 may have a length selected to match or exceed the length of the pin sleeve 122, to be described below, so as to provide suitable length for crimping the inner coil conductor 120. Other conductor end lengths may be selected and a suitable length of the cavity 172 may be selected to ensure sufficient crimp length of the coil 120 within the cavity 172.

The conductor end 162 may include a hole or a pair of holes 174 for inspecting the crimped inner coil conductor 120 within the cavity 172. The holes 174 may extend through the conductor end 162 from an outer surface and into the cavity 172 and may be positioned near a proximal end of the cavity 172. As such, when the conductor 120 is crimped in the cavity 172, a portion of the inner coil conductor 120 may be visible through the hole or holes 174 and the depth into the cavity 172 of the crimp connection may be ascertainable to assure sufficient crimp length.

The connector pin 112 can be made from one or more of several biocompatible conductor materials such as stainless steel 316L or a metal alloy, MP35N, for example. The pin material may be selected to be biocompatible and suitably conduct and transmit electrical signals from an electrical stimulation device. The material, together with the sizes of the pin 112 and the pin sleeve 122 (e.g., relative diameters and wall thicknesses), may be selected to suitably crimp the inner conductor or coil 120 therebetween such that a reliable crimp connection is provided that is both mechanically secure and through which electrical transmissions can be made. It is noted that the connector pin 112 may be engineered to have sufficient strength to withstand compression forces associated with assembly. For example, as can be appreciated from FIG. 2, the conductor end 162 of the pin 112 may be forced through the bore 118 of the connector insulator 116 into the bore 119 and the necked down portion 164 of the pin 112 may be suitably strong to withstand such a compression force without buckling or weakening. In an effort to more smoothly insert the pin 112, the distal end of the conductor end 162 may include an exterior taper 176 as shown in FIG. 3.

Figure 4:
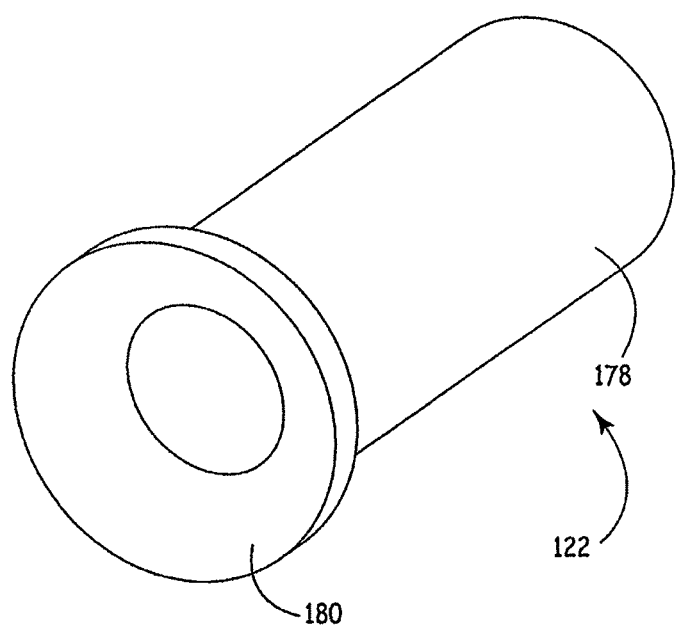
FIG. 4 is an isometric view of a pin sleeve of the lead of FIGS. 1 and 2.

An isolated view of the pin sleeve 122 is shown in FIG. 4. The pin sleeve 122 may be adapted for insertion a selected distance into the proximal end of the conductor or coil 120. As such, the pin sleeve 122 may include a sleeve portion 178 and a flare portion 180. The sleeve portion 178 may be substantially cylindrically shaped for insertion into the proximal end of the inner coil conductor 120. The diameter of the sleeve portion 178 may be slightly larger than that of the inner coil conductor 120 to create some connecting friction between the sleeve 122 and the inner coil conductor 120 when the coil is sleeved over the sleeve portion 178. The diameter of the pin sleeve 122 may also be selected to suitably pinch or press the inner coil conductor 120 against the inner surface of the cavity 172 of the conductor end 162 of the pin 112 when crimping the inner coil conductor 120.

The sleeve portion 178 may have a length selected to sufficiently engage the coil 120 and hold the inner coil conductor 120 when the inner coil conductor 120 is crimped between the sleeve 178 and the inner surface of the conductor end 162 of the pin 112. The flare portion 180 of the sleeve 122 may be positioned on a proximal end of the sleeve 122 and may be configured to limit or stop the insertion distance of the sleeve 122 in the inner coil conductor 120 and to prevent the sleeve 122 from passing too far into the coil 120 when crimping the inner coil conductor 120. As such, the flared portion 180 may define a gradually increasing diameter beginning with the diameter of the sleeve portion 178 and extending to a diameter approximating the inner diameter of the crush cavity 172 of the conductor end 162 of the pin 112. It is noted that the proximal end of the pin sleeve 122 is shown as a flared portion in contrast to the more square or flange-like proximal end on the ring sleeve 136 of FIGS. 8A and 8B. The shape of the proximal ends of these parts 122, 136 may be selected based on whether the respective part is formed from tubing or bar stock.

For example, if the part is formed from tubing, the proximal end may be flared like the pin sleeve 122 shown. However, if the part is formed from bar stock, the proximal end may be flanged like the ring sleeve 136. Other fabrication techniques and approaches may also be used.

The inner diameter of the conductor end 162 of the pin 112 and the outer diameter of the sleeve portion 178 of the pin sleeve 122 may be selected to suitably crimp the inner conductor or coil 120 therebetween. For example, the pin sleeve 122 may have an outer diameter and the wire used for the inner coil 120 may have a thickness. The inner diameter of the cavity 172 may be selected to be slightly less than the outer diameter of the pin sleeve 122 plus twice the wire thickness. As such, when the pin sleeve 122 is inserted into the coil 120 and the pin sleeve 122 and conductor 120 are pressed into the cavity 172 of the conductor end 162 of the pin 112, the coil 120 may be crimped between the pin sleeve 122 and the inner surface of the cavity 172 of the conductor end 162 of the pin 112. Consideration may be given to the thicknesses and elasticity of the conductor end 162 of the pin 112 and the sleeve 122 when selecting suitable relative diameters.

The inner conductor or coil 120 may be an electrically conductive member extending longitudinally along the lead 100. The conductor 120 may be in the shape of a coil or a tubular sleeve shape may be provided. The coil shape may provide flexibility to the lead and allow for maneuverability when placing the lead, for example. The inner conductor 120 may define a longitudinally extending bore along its length for receiving a stylet or other device.

As mentioned, the inner parts may be electrically isolated from the outer parts by a system of insulating parts. A close-up view of the connector insulator 116 is shown in FIGS. 5A and 5B. The connector insulator 116 may be configured for sleevably isolating the connector pin 112 and a portion of the inner conductor 120 from the outer parts. In addition, the connector insulator 116 may be configured for supporting a portion of the proximal seal 114. The connector insulator 116 may include a central body 182, a proximal extension 184, and a distal extension 186. The central body 182 may include a substantially cylindrically shaped body having an outer diameter. The distal extension 186 may also be substantially cylindrically shaped and may include an outer diameter smaller than that of the central body 182.

The distal extension 186 may extend from the central body 182 in the distal direction from a set of cascading shoulders 188, 190. An outer shoulder 188 may be defined by the interface of a portion of the outer surface 129 of the central body 182 and a step surface 132. The inner width 190 may be defined by a cylindrical inner shoulder surface 127 intersecting normally with the step surface 132 and transitioning to an additional radially oriented step surface 128. The width of the step surface 132 may define the difference between a diameter of a cylindrical inner shoulder surface 127 and the diameter of the central body. The diameter of the inner shoulder surface 127 is less than the diameter of the central body 182 but larger than the diameter of the distal extension 186. The width of the additional step surface 128 may define the difference between the diameter of the inner shoulder surface 127 and the diameter of the distal extension 186.

The distal tip of the distal extension 186 may include a tapered or chamfered tip 189 creating a conical shape for receiving a dilated portion 126 of the insulator tubing 124. As shown in FIG. 2, for example, the dilated portion 126 of the insulator tubing 124 may be stretched, expanded, or otherwise distended over the distal extension 186 of the connector insulator 116. However, once placed over the distal extension 186, the elasticity of the material of the insulator tubing 124 causes the insulator tubing 124 to compress around the distal extension 186 to create a fluid-tight, compression fit between the insulator tubing 124 and the connector insulator 116 to electrically isolate the inner conductor 120. The dilated portion 126 is held away from the crimp connection of the inner conductor 120 to provide space for this connection and may help to avoid binding, pinching, or otherwise constricting the crimp connection at this location.

The proximal extension 184 of the connector insulator 116 may extend from the proximal end of the central body 182 and may be substantially cylindrical with a diameter smaller than that of the central body 182. The transition between the central body 182 and the proximal extension 184 may define a proximal shoulder 183 opposite the cascading shoulders described. The interface between the proximal extension 184 and the proximal shoulder 183 may be formed as a small, concave, annular radius 185. The proximal extension 184 may extend partially underneath the proximal seal 114. As such, when the proximal seal 114 is positioned on the proximal extension 184 a distal end of the proximal seal 114 may abut the proximal shoulder 183 of the central body 182 and the proximal end of the connector insulator 116 may align with a shoulder 197 within a center bore 150 of the proximal seal 114 as shown in FIGS. 2 and 6B.

The connector insulator 116 may include center bore 118 with a diameter configured for receiving the bar portion 164 of the connector pin 112. The center bore 118 may extend from the proximal end of the insulator 116 to a point within the central body 182 of the insulator 116 where the center bore 118 may transition to a bore 119 with a larger diameter. The bore 119 with the larger diameter may accommodate the increased diameter of the conductor end 162 of the connector pin 112. The diameter of the bores 118, 119 may closely fit the respective portions of the connector pin 112. The bore 119, with its larger diameter, may extend through the remaining portion of the central body 182 and through the distal extension 186 of the connector insulator 116.

The connector insulator 116 may be constructed from a bio-compatible grade of insulator material. This material may be selected to provide sufficient mechanical strength, elasticity, and insulation characteristics. For example, as described with respect to the connector pin 112, the conductor end 162 of the connector pin 112 may be pressed through the bore 118 of the connector insulator 116. As such, the connector insulator 116 may be made of a relatively strong yet elastic material allowing the pin 112 to be driven therethrough without loss of strength and without permanent deformation. In some embodiments, the connector insulator 116 may be made from a moldable thermoplastic such as polyurethane, polysulfone, or PEEK. Still other material may be selected to provide the suitable strength, elasticity, and insulation characteristics.

While elastic, the connector insulator 116 may also be designed to secure the connector pin 112 and prevent the connector pin 112 from being removed or withdrawn from the proximal end of the lead 100. A proximal shoulder 131 at the proximal end of the conductor end 162 may be provided to transition to the smaller diameter necked down portion 164 (See FIG. 3.). A surface 135 of the shoulder 131 may interact with an opposing surface 137 of shoulder 133 on the interior surface of the connector insulator 116. (See FIG. 2.) The shoulder 133 on the interior of the connector insulator 116 may be formed as the transition between the bore 118 and bore 119. The relative diameters of the bar portion 164 and bore 118 and the relative diameters of the conductor end 162 and bore 119 may be selected to allow the connector pin 112 to rotate within the connector insulator 116. However, to prevent removal therefrom, the diameter of the conductor end 162 may be selected to be larger than the diameter of the bore 118. In addition, the material of connector insulator 116 may be selected to be rigid enough to prevent withdrawal of the connector pin 112 under withdrawal loads or strengths specified by the IS-1 specification, for example.

The proximal seal 114 may be configured for secured placement on the connector insulator 116 and for sealingly engaging a socket on an electrical stimulation device. In addition, the proximal seal 114 may function, together with the connector insulator 116, to electrically isolate and prevent crosstalk between the ring connector 130 and the connector pin 112. As shown in FIGS. 6A and 6B, the proximal seal 114 may include a flush portion 198 and a seal portion 199. The flush portion 198 may be distal to the seal portion 199 and may function to encompass the proximal extension 184 of the connector insulator 116 and abut the central body 182 thereof. The flush portion 198 may be substantially cylindrical with an outer diameter substantially matching the outer diameter of the central body 182 of the connector insulator 116 thereby being flush therewith. The seal portion 199 may be proximal to the flush portion 198 and may also be substantially cylindrical with an outer diameter slightly larger than the flush portion 198. The seal portion 199 may include one or more (e.g., two) annular, radially-extending ribs 196 protruding from the outer surface of the seal portion 199 and defining relatively deep channels 195 in between. The ribs 196 may extend from the seal portion 199 such that the outer surface or tip of the ribs 196 defines a diameter larger than the flush portion 198. The diameter of the channels 195 may be smaller than the diameter of the flush portion 198 such that there is a stepped shoulder 195 between a base wall 193 of the channel 195 and the flush portion 198. A proximal annular lip 191 of the proximal seal 114 may have a similar diameter to the diameter of the channels 195 at the base wall 193 and may extend proximally as an annular ring from the most proximal rib 196. The ribs 196 may be adapted to engage a cylindrical socket and may have an outer diameter at least slightly larger than the diameter of the socket so as to sealingly engage an inner surface of the socket and prevent fluids or other matter from traveling into the socket and reaching the connector pin 112 or otherwise leaking into the electrical stimulation device.

The proximal seal 114 may include a bore 150 extending from the proximal end that expands to form a larger diameter distal bore 151 at the distal end. The smaller diameter bore 150 may be sized to seal against the outer diameter of the bar portion 164 of the connector pin 112. The bar portion 164 may further be fixed to an inner surface 156 of the bore 150 by a medical adhesive or other bio-adaptable adhesive equivalent. A squared shoulder 197 may be formed by the step in diameter between the bore 150 and the distal bore 151.

The diameter of the distal bore 151 may be substantially equal to the outer diameter of the proximal extension 184 of the connector insulator 116. When inserted within the distal bore 151, the proximal extension 184 may abut and seal against the squared shoulder 197. In some embodiments, the proximal seal 114 may be made of a resilient material and the diameter of the distal bore 151 may be slightly smaller than the outer diameter of the proximal extension 184 of the connector insulator 116 such that the proximal seal may be stretched to receive the connector insulator 116 thereby compressively receiving the connector insulator 116 therein. The proximal seal 114 may be made from a suitably resilient material to compressively seal the proximal end 102 of the lead 100 with the electrical stimulation device. In some embodiments, the seal 114 may be a biocompatible silicone, for example. Still other materials may be selected to suitably seal the proximal end 102 of the lead 100 with the electrical stimulation device and also be compatible with the body.

The insulator tubing 124 shown in FIG. 2 may function to electrically isolate portions of the inner parts from the outer parts. Along some portions of the lead 100, the insulator tubing 124 may function together with the connector insulator 116 to provide the electrical isolation. As shown, conductive portions of each of the inner parts, including the conductor end 162 of the connector pin 112, the inner coil 120, and the pin sleeve 122, may be separated from the outer parts by the inner insulator tubing 124. Near the proximal end of the conductor 120, the distal extension 186 of the connector insulator 116 also isolates these elements. The insulator tubing 124 may be substantially tube-like in shape defining an inner lumen having a diameter slightly larger than the outer diameter of the inner conductor or coil 120. The insulator tubing 124 may be made of an insulating material so as to electrically isolate the enclosed components or features from the components or features outside the tubing 124. The material of the insulator tubing 124 may further be chosen to have resilient elastic properties in order to create compression connections with other components. In one implementation, the insulator tubing 124 may be a silicon tube.

The insulator tubing 124 may have a dilated or flared portion 126 at its proximal end for receiving the distal extension 186 of the connector insulator 116. In some embodiments, the flared portion 126 may be chemically and mechanically dilated or expanded to fit over the distal extension 186 of the connector insulator 116. The resilient, elastic properties of the insulator tubing 124 result in the insulating tubing 124 compressing about the connector insulator 116 after dilation and creating a fluid-tight, compression fit therebetween to electrically isolate the inner conductor 120. The flared portion 126 may be held open by the distal extension 186 of the connector insulator 116 and may help to prevent binding of the inner parts by providing space for the crimp connection. Within the distal extension 186 of the connector insulator 116, the conductor end 162 of the pin connector 112, the pin sleeve 122, and the proximal end of the inner conductor or coil 120 may be arranged and thus electrically isolated from components or features outside the flared portion 126.

Having described the inner parts and the isolation thereof by the insulator tubing 124 and the connector insulator 116, the outer parts may now be described. As shown in FIG. 2, the outer parts may include the ring connector 130, an outer conductor or coil 134, and a ring sleeve 136.

The ring connector 130 may be configured to provide an exposed surface for electrical communication with an electrical stimulation device. The ring connector 130 may also be configured for axially and rotationally securing the outer parts to the connector insulator 116.

Figure 7B:
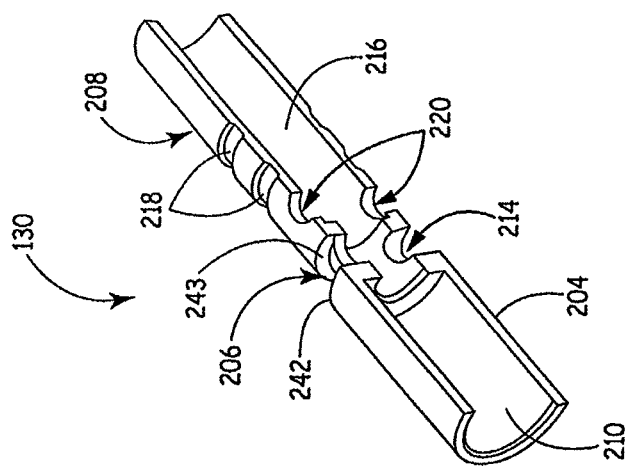
FIGS. 7A and 7B are an isometric view and an isometric cross-sectional view, respectively, of a ring connector of the lead of FIGS. 1 and 2.
Figure 7A:
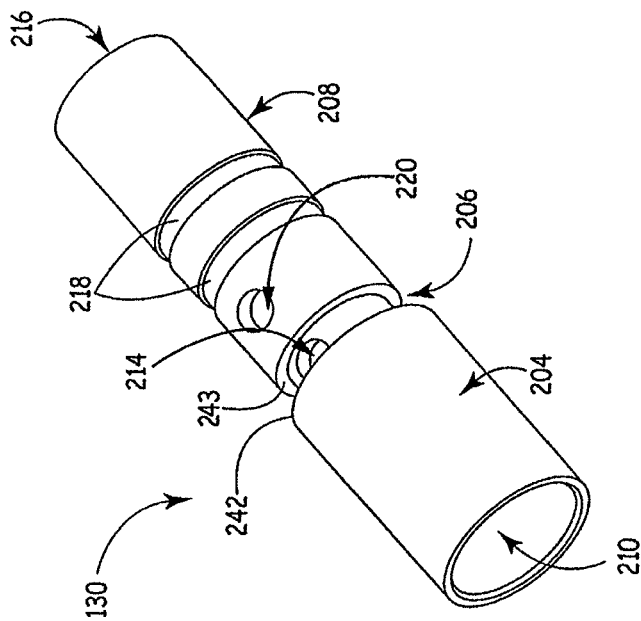

A close-up view of the ring connector 130 is shown in FIGS. 7A and 7B. The ring connector 130 may include a band portion 204, a slot portion 206, and a crimp portion 208. The band portion 204 may form an exposed conductive band near the proximal end 102 of the lead 100 that is distal to the connector pin 112. The band portion 204 may be configured for electrical communication with a portion of a socket of an electrical stimulation device and the diameter of the band portion 204 may be selected to suitably engage electrical conductors within the socket.

The band portion 204 may be substantially cylindrical in shape with an outer diameter matching that of the central body 182 of the connector insulator 116. The band portion 204 may define an inner cavity 210 configured to receive the distal extension 186 of the connector insulator 116. More particularly, the inner cavity 210 of the band portion 204 may have a diameter substantially equal to or slightly smaller than the outer diameter of the cylindrical inner shoulder surface 127 on the connector insulator 116. As such, the band portion 204 may be sleeved over the portion 126 positioned on the distal extension 186 and may frictionally engage the cylindrical inner shoulder surface 127 to secure the ring connector 130 to the connector insulator 116. In this manner, the concentric assembly of the several parts of the system may be maintained. The proximal edge of the band portion 204 of the ring connector 130 may thus abut the step surface 132 of the connector insulator 116 causing the outer surface of the band portion 204 to be flush with the central body 182 of the connector insulator 116. The band portion 204 may have a length slightly greater than the length of the distal extension 186 of the connector insulator 116.

The slot portion 206 of the ring connector 130 is distal relative to the band portion 204 and is positioned intermediate the band portion 204 and the crimp portion 208. The slot portion 206 may be substantially cylindrical in shape with a diameter smaller than the band portion 204. The slot portion 206 may have an inner diameter similar to or slightly larger than the outer diameter of the insulator tubing 124, whereby the slot portion 206 is configured to engage in a fluid-tight fit with the insulator tubing 124. The outer diameter of the slot portion 206 may allow for an inwardly projecting rib 143 from the boot seal 140 to nest therein as further described below. The rib 143 may be held in position longitudinally by two opposing surfaces 242 and 243 defining the boundaries of the slot portion 206. The slot portion 206 may include one or more holes 214 for introduction of adhesive to secure the ring connector 130, the insulator tubing 124, and the boot seal 140 together.

The crimp portion 208 may be arranged distally to the slot portion 206 and may be substantially cylindrical in shape with an outer diameter larger than the slot portion 206 and smaller than the band portion 204. Like the conductor end 162 of the connector pin 112, the crimp portion 208 of the ring connector 130 may be configured for crimping of the outer conductor 134 therein. As such, the crimp portion 208 may define a crimp zone or cavity 216 therein. The cavity or crimp zone 216 may include an inner diameter selected in conjunction with the ring sleeve 136 to suitably crimp the outer conductor 134 therein. That is, the ring sleeve 136 may have an outer diameter and the outer conductor 134 may include a wire thickness. The inner diameter of the crimp zone or cavity 216 may be selected to be equal to or slightly smaller than the outer diameter of the ring sleeve 136 plus twice the wire thickness, for example.

Like the inner conductor crimp connection, the material strength, diameter, thickness, and elasticity may be considered when selecting the relative diameters for crimping the outer conductor 134. The crimp portion 206 of the ring connector 130 may have a length equal to or slightly larger than the ring sleeve 136 such that a sufficient length of the outer conductor 134 may be crimped therein. In some embodiments the crimp portion 208 of the ring connector 130 may include circumferentially extending grooves 218 extending around its circumferential outer surface for engagement with the boot seal 140. The crimp portion 208 may also include a hole or a pair of holes 220 for inspecting the crimped conductor 134 within the cavity 216 and confirming the quality of the connection. The holes 220 may extend through the crimp portion 208 from an outer surface and into the cavity 216 and may be positioned near a proximal end of the cavity 216. As such, when the conductor 134 is crimped in the cavity 216, a portion of the conductor 134 may be visible through the hole or holes 220 and the crimp connection may be ascertainable to assure sufficient crimp length. The holes 220 may also provide for an adhesive reservoir to help bond the boot seal 140 to the ring connector 130.

Like the connector pin 112, the ring connector 130 may be constructed of a bio-compatible conductive material. For example, the ring connector 130 may be made from stainless steel 316L or a metal alloy MP35N. Other materials may also be used and may be selected to provide suitable biocompatibility and conductivity. Additionally, as with the connector pin 112, the material and dimensions (e.g., relative diameters and wall thicknesses) may be selected to suitably allow for a crimp connection to the outer conductor or coil 134 that is both mechanically secure and also effectively transmits electrical signals.

The outer conductor or coil 134 may be the same or similar to the inner conductor or coil 120. However, the outer conductor or coil 134 has a diameter larger than the inner conductor or coil 120. The diameter of the outer conductor or coil 134 may be selected such that the inner conductor or coil 120 and the insulator tubing 124 may be received therein. As such, the outer conductor or coil 134 may have a diameter equal to or slightly greater than an outside diameter of the inner conductor or coil 120 plus twice the thickness of the insulator tubing 124.

The ring sleeve 136, like the pin sleeve 122 may be configured for crimping the outer conductor or coil 134 within the crimp portion 208 of the ring connector 130. As shown in FIGS. 8A and 8B, the ring sleeve 136 may be formed as a cylindrical sleeve portion 222 with a flare or flange portion 224 for controlling the depth within the coil 134 that the ring sleeve 136 extends. The sleeve portion 222 may be substantially cylindrical with an outer diameter slightly larger than an inner diameter of the outer coil 134. As such, when inserted into a proximal end of the outer coil 134, some frictional engagement between the ring sleeve 136 and the outer coil 134 may be provided. The flare or flange portion 224 may be positioned on the proximal end of the sleeve portion 222 and may have an outer diameter larger than that of the sleeve portion 222 for abutting the end of the outer conductor or coil 134 and resisting advancement of the ring sleeve 136 beyond the proximal end of the outer conductor or coil 134. The diameter of the flare or rib 224 may be selected to be slightly less than the inner diameter of the crimp portion 208 of the ring connector 130 so as to avoid inhibiting the pinching or crimping of the coil 134 between the sleeve portion 222 and the inner surface of the crimp portion 208 of the ring connector 130. As discussed with respect to the pin sleeve 122, the shape of the proximal end of the pin sleeve 122 and the ring sleeve 136 may depend in part on the type of raw material used to form the respective part. For example, if tubing is used, the proximal end may be flared, while, if bar stock is used, the proximal end may be more square in cross-section or flange-like. Other geometries may also be provided to stop the sleeves from advancing too far into the proximal end of the respective coils 120, 134.

Figure 9A:
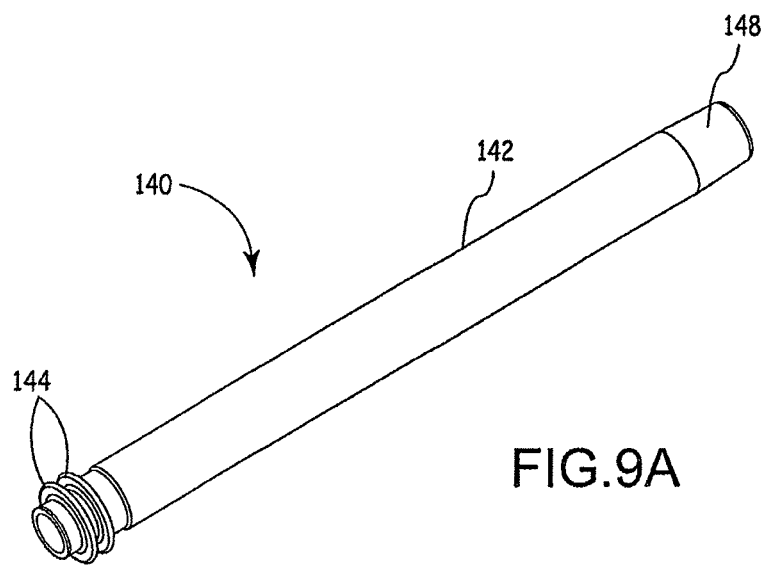
FIGS. 9A and 9B are an isometric view and an isometric cross-sectional view, respectively, of a boot seal of the lead of FIGS. 1 and 2.
Figure 9B:
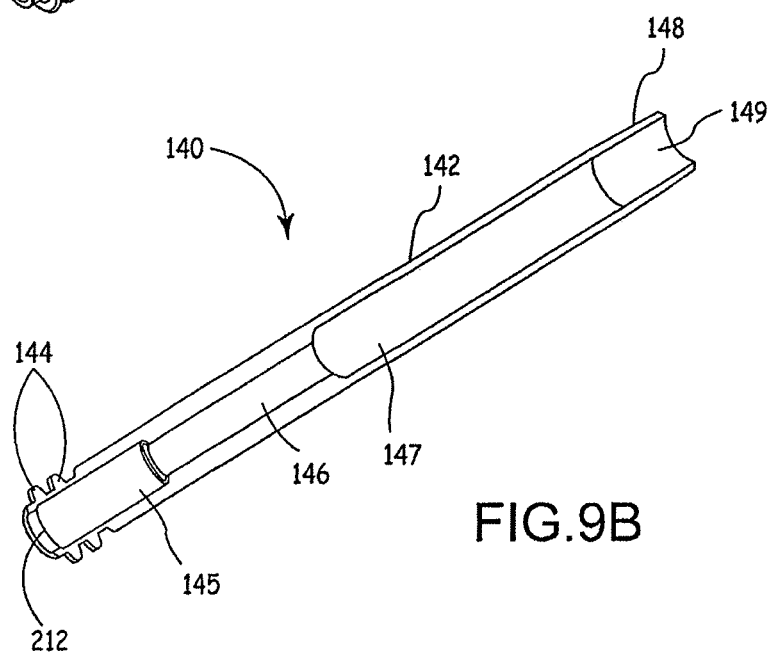

The boot seal 140 is shown in FIGS. 9A and 9B. The boot seal 140 may be configured for encompassing and sealing against the distal end of the ring connector 130 and the proximal end of the outer sheath 152 to prevent entry of fluids. For example, when the proximal end 102 of the lead 100 is inserted into a socket of an electrical stimulation device, the boot seal 140 may prevent fluids or other material from entering the socket and interfering with the ring connector 130 or other portions of the electrical stimulation device. As such, the boot seal 140, like the proximal seal 114, may have one or more annular, radially-extending sealing ribs 144 protruding from its outer surface at its proximal end. The sealing ribs 144 may be adapted to engage a cylindrical socket and may have an outer diameter at least slightly larger than the diameter of the socket so as to sealingly engage an inner surface of the socket and prevent fluids or other matter from traveling into the socket and reaching the ring connector 130 or otherwise leaking into the electrical stimulation device. The boot seal 140 may be relatively long with a cylindrical shaft portion 142 that extends distally from the sealing ribs 144 and may provide a grip for the surgeon or other installer for handling the proximal end 102 of the lead 100. The cylindrical shaft portion 142 may taper radially inward at the distal end of the boot seal 140 to form a chamfered portion 148.

The boot seal 140 may define a bore 141 extending from its proximal end to its distal end. The diameter of the bore may vary along the length of the seal 140. The diameter of a proximal section 145 of the bore 141 may be sized to house the crimp portion 208 of the ring connector 130. Moving distally, the diameter of the bore 141 throughout a medial section 146 may be reduced and may be sized just slightly larger than the outer diameter of the outer coil 134. Moving still further distally, the diameter of a distal section 147 of the bore 141 may again be enlarged with respect to the medial section 146. In this distal bore section 147, the boot seal 140 may be enlarged to receive the outer insulating sheath 152 and for the application of a lead label and/or serial number. The bore 141 within the chamfered portion 148 at the distal end of the boot seal 140 may also be tapered slightly radially inward to form a tapered seal portion 149 that creates the fluid tight seal around the outer sheath 152. The proximal end of the boot seal 140 may define an annular securing rib 143 protruding inwardly for positioning in the slot portion 206 of the ring connector 130, thereby securing the axial position of the boot seal 140. Like the proximal seal 114, the boot seal 140 may be made from a biocompatible silicone to resiliently engage and seal the lead 100 relative to the electrical stimulation device. Other materials may also be used.

Referring again to FIG. 2, the assembled proximal end of the lead may be described. As shown, the electrically conductive connector pin 112 may extend through and may be disposed in a center bore 150 of a proximal seal 114 and a center bore 118 of a connector insulator 116. The bar portion 164 of the connector pin 112 may be arranged in the center bore 118. A distal part of bar portion 164 may be separated from the inner surface of the center bore 150 by the proximal extension 184 of the connector insulator 116. The electrically conductive inner conductor or coil 120 may be crimped to the conductor end 162 of the connector pin 112 in conjunction with the pin sleeve 122. The inner insulator tubing 124 may extend over the inner coil conductor 120 and the flared portion 126 thereof may be sleeved onto the distal extension 186 of the connector insulator 116 to create a fluid-tight, compression fit therewith. The inner insulator tubing 125 may abut the inner shoulder 190 of the cascading shoulders and having an outer surface substantially flush with the cylindrical outer surface 127 of the inner shoulder 190. As such, the connector pin 112, the crimp connection, and the inner coil 120 may be substantially fully insulated along its length by the connector insulator 116 and the insulator tubing 124. However, the inner conductor 120 may be exposed via an electrode at the distal end 104 for treatment and the connector pin 112 may be exposed at the proximal end 102 for electrical communication with an electrical stimulation device. The proximal seal 114 may be arranged on the connector insulator 116 and the outwardly projecting ribs 196 may engage a socket on an electrical stimulation device to prevent fluid or other liquid from contacting with the connector pin 112.

The band portion 204 of the ring connector 130 may extend over the flared portion 126 of the insulator tubing 124 and may abut the outer shoulder 188 of the cascading shoulders on the connector insulator 116. As shown, the outer surface of the band portion 204 of the ring connector 130 may be flush with the outer surface 129 of the central body 182 of the connector insulator 116. The outer conductor or outer coil 134 may be arranged to sleevably receive the inner coil 120 and insulator tubing 124. The outer conductor or coil 134 may be crimped to the ring connector 130 by a ring sleeve 136, thereby electrically connecting to the ring connector 130. The boot seal 140 may be positioned over the outer coil 134 and an inwardly protruding rib 143 thereof may engage a slot portion 206 of the ring connector thereby securing the position of the boot seal 140 relative to the ring connector 130. The crimped outer coil 134 and portions of the ring connector 130 may be disposed within a center bore 141 of the boot seal 140. Like the proximal seal 114, the radially projecting ribs 144 of the boot seal 140 may engage a socket on an electrical stimulation device to prevent body fluid or other liquid from contacting the ring connector 130 or otherwise entering the electrical stimulation device.

Accordingly, the connector pin 112 may be electrically connected to the inner coil 120, and the ring connector 130 may be electrically connected to the outer coil 134. In operation of the lead, electrical signals may be sent from the proximal end 102 to the distal end 104 via the connector pin 112 and the inner coil 120, and via the ring connector 130 and the outer coil 134. The inner coil 120 may be electrically insulated from the outer coil 134 by the inner insulator tubing 124. The ring connector 130 may be electrically insulated from the inner coil 120 by the inner insulator tubing 124 and the connector insulator 116. The connector pin 112 may be electrically insulated from the ring connector 130 by the proximal seal 114 and the connector insulator 116. The connector pin 112 may be prevented from contacting fluid or other liquid by the sealing ribs 196 of the proximal seal 114. The ring connector 130 may be prevented from being in contact with fluid or other liquid by the sealing ribs 144 of the boot seal 140.

The passive tip 108 at the distal end 104 of the lead 100 is depicted in cross section in FIG. 10. The passive tip 106 may be considered to be composed primarily of a ring electrode 103, a tip electrode 105, and a passive tip sheath 108. A proximal end of the ring electrode 103 is electrically and mechanically connected to the distal end of the outer conductor coil 134. The proximal end of the tip electrode 105 is electrically and mechanically connected to the distal end of the inner conductor coil 120. The distal end of the ring electrode is connected to the proximal end of the passive tip sheath 108. The proximal portion of the tip electrode is substantially encased within the passive tip sheath 108 with the exception of an annular tip face 308 that is exposed and abuts a distal end of the passive tip sheath 108.

Figure 11A:
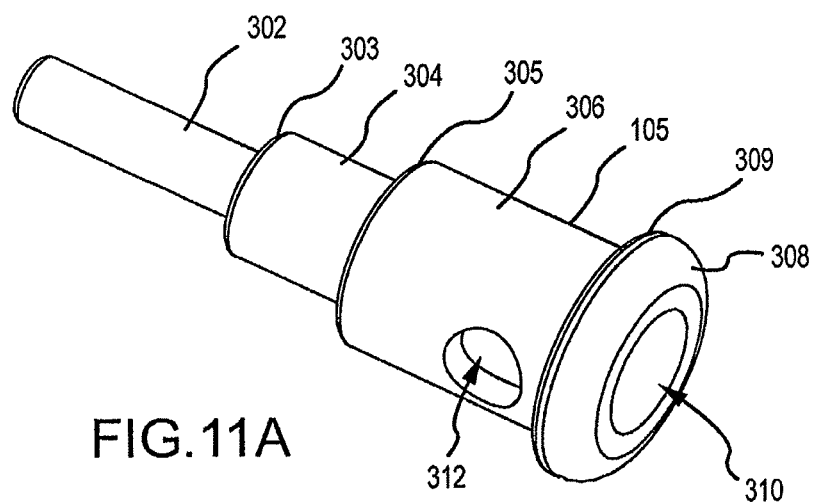
FIGS. 11A and 11B are an isometric view and an isometric cross-sectional view, respectively, of a tip electrode of the lead of FIGS. 1, 10A, and 10B.
Figure 11B:
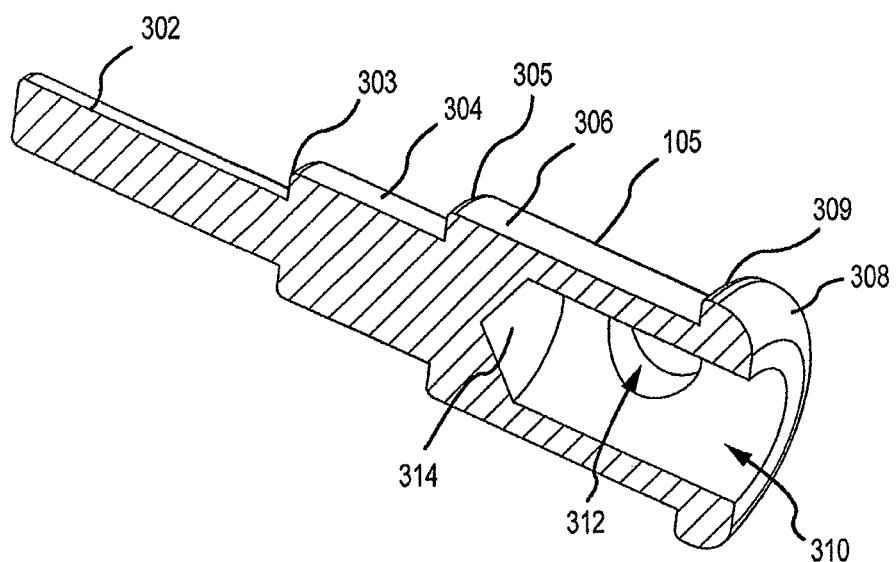

The tip electrode 105 is depicted in greater detail in FIGS. 11A and 11B. The tip electrode may be generally cylindrical in shape with a number of stepped outer diameters, beginning at the proximal end with a proximal shaft section 302 of the smallest diameter. The proximal shaft section 302 is the section of the tip electrode 105 that engages the inner conductor coil 120 as will be described in further detail below. The proximal shaft section 302 transitions into a larger diameter medial shaft section 304 at a medial shoulder 303. The medial shaft section 304 may further transition distally into an even larger outer diameter barrel section 306 at a barrel shoulder 305, which is the section of the tip electrode 105 that may interface with an annular shelf 337 of the passive tip sheath 108 to help retain the passive tip sheath 108 on the lead 100. The barrel section 306 may further transition to the annular tip face 308 having and even larger outer diameter at a tip shoulder 309. The annular tip face 308 may be exposed to the patient's blood and tissue when the lead 100 is implanted in vivo. The electrode tip 105 may thus be made of a precious metal, for example, Pt/Ir, Pt, or another electrically conductive, biocompatible material. The tip shoulder 309 may further interface with an annular face 325 of the passive tip sheath 108 to additionally help retain the passive tip sheath 108 on the lead 100.

The outer surface of the tip face 308 may be formed as a radiused curve from the tip shoulder 309 to a point at which an entrance to a steroid cavity 310 within the barrel section 306 is defined. The steroid cavity 310 may be generally cylindrical as it extends within the barrel section 306. In the exemplary embodiment shown in FIG. 11B, the base wall 314 of the steroid cavity 310 may be formed a concave conical surface. The sidewalls of the barrel section 306 may define one or more (in this example, two) adhesive apertures 312 for introduction of adhesive through the steroid cavity 310 onto the outer surface of the barrel portion 306 to create an adhesive bond with the passive tip sheath 108. Adhesive may also be provide in the concave are formed in the based wall 314 in the steroid cavity 310 in order to assist in retaining the steroid 107 therein.

One exemplary embodiment of a passive tip sheath 108 is depicted in greater detail in FIGS. 12A and 12B. The passive tip sheath 108 may be generally cylindrical in shape with a long tubular sheath 320 forming the proximal section thereof. The tubular sheath 320 may transition at a stepped shoulder 321 to a narrower diameter tine recess section 322. Immediately distal to the tine recess section 322 is a tine section 323 from which a plurality of tines 110 (in this exemplary embodiment, four) protrude at a number of evenly-spaced circumferential locations about the tine section 323. The tines 110 extend proximally from the tine section 323 at an acute angle with respect to the recess section 323. The passive tip sheath 108 may extend a short length further distally from the tine section 323 in a sloped section 324 that tapers in diameter until terminating at an annular face 325.

The tines 110 may be integrally formed with the passive tip sheath 108 and may flex at the interface with the tine section 323 in the manner of a living hinge. The tines 110 may flex radially inward and fold flat against the recess section 322 such that the outer diameter across the recess section 322 when the tines 110 are folded down is substantially the same as the outer diameter of the tubular sheath 320. In this manner, when the lead 100 is advanced through a catheter for in vivo placement, the tines 110 can fold against the recess section 322 and the passive electrode tip 106 can easily pass through a delivery catheter. When the passive electrode tip 106 emerges from the distal end of the delivery catheter, the tines will spring radially outward and provide anchor structures to anchor the distal end 104 of the lead 100 in cardiac tissue. The passive tip sheath 108 may be formed of a resilient biocompatible elastomeric material in order to both provide for the resilient properties needed for the tines 110 and to be fitted over the tip electrode 105 and other structures and retained thereon.

The passive tip sheath 108 may define a lumen 326 therethrough in order to be fitted over the tip electrode 105, a length of the inner coil 120, and the distal end of the ring electrode 103 as will be further described herein in greater detail. At a proximal end, the lumen may define a sleeve bore 328 of relatively large diameter with respect to the rest of the lumen 326 that is sized in both diameter and length to sleeve over and create a fluid-tight connection with the connection section 360 of the ring electrode 103. The sleeve bore 328 transitions at a sleeve shoulder 329 to a relatively long inner coil bore 330 of a narrower inner diameter that is sized to extend over the inner conductor coil 120 for a length until the inner conductor coil 120 couples with the tip electrode 105. The inner coil bore 330 transitions to a middle bore 332 of larger inner diameter along a sloped section 331 that gradually increases the inner diameter between the two bore sections. The middle bore 332 is sized in diameter and length to fit about a connection between the connection between the outer insulating tubing 124 and the proximal end of the tip sleeve 109.

The middle bore 332 transitions to a tip sleeve bore 334 of smaller diameter at a squared shoulder 333, that abuts a distal end of the outer insulating tubing 124. The tip sleeve bore 334 covers the remainder of the tip sleeve 109 that forms a crimp connection with the tip electrode 105. The tip sleeve bore 334 then transitions to a tine bore 336, which is generally coextensive with the tine section 323 on the outer surface of the passive tip sheath 108 and which houses the medial shaft section 304 of the tip electrode 105. Finally, the lumen 326 exits the distal end of the passive tip sheath 108 through a tip bore 338 that is of a larger diameter than the tine bore 336 and which is sized to house the barrel section 306 of the tip electrode 105. The annular shelf 337 acts as a shoulder at the change in diameter between the tine bore 336 and the tip bore 338. The annular shelf 337 acts as an axial stop abutting the tip shoulder 309 of the tip electrode 105 to prevent the passive tip sheath 108 from sliding distally off of the lead 100.

Figure 26A:
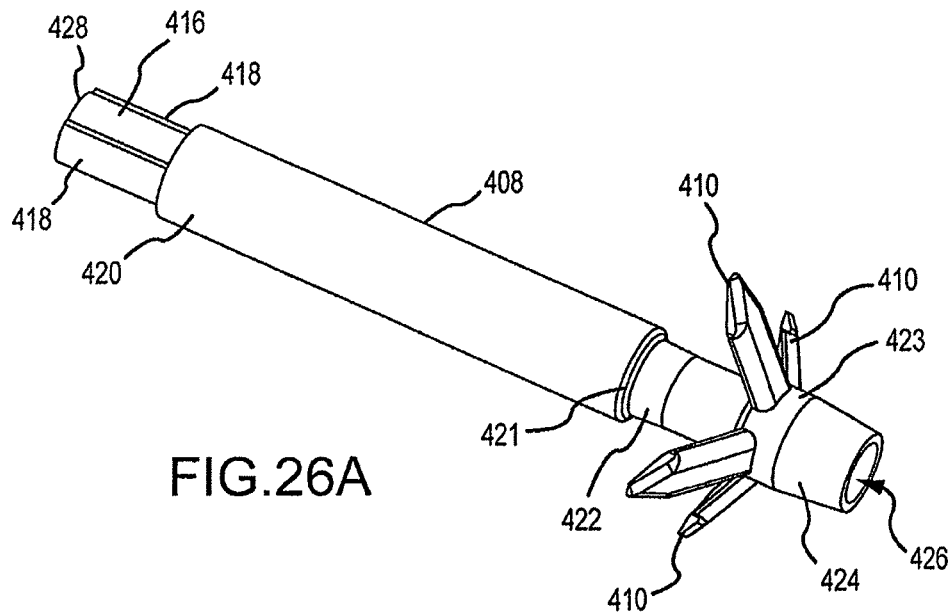
FIGS. 26A and 26B are an isometric view and an isometric cross-sectional view, respectively, of an alternate embodiment of a passive tip sheath for use in the lead of FIGS. 1, 10A, and 10B.
Figure 26B:
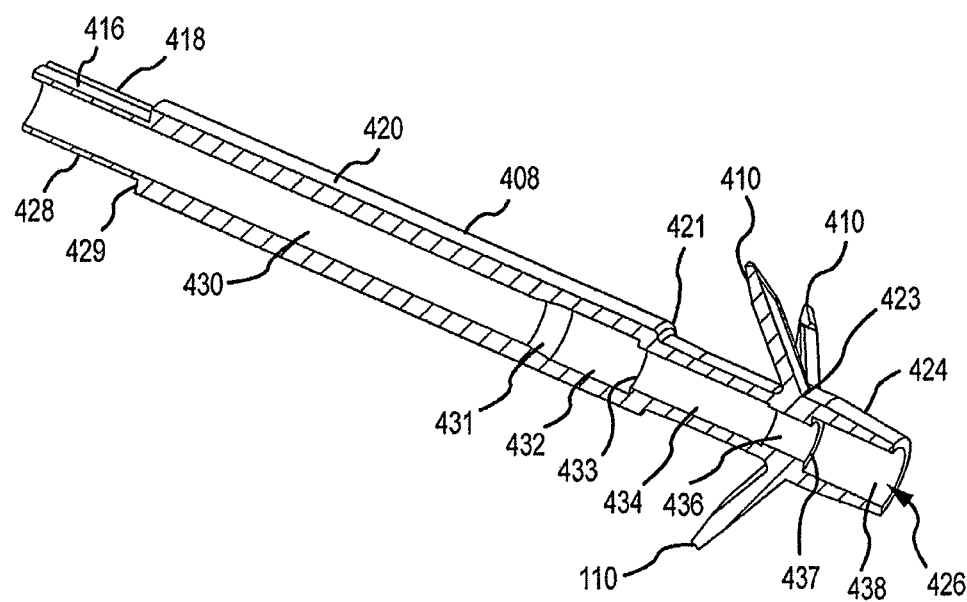

Another exemplary embodiment of a passive tip sheath 408 is depicted in greater detail in FIGS. 26A and 26B. It is in many respects similar to the passive tip sheath 108 of FIGS. 12A and 12B except for the proximal end. For example, the passive tip sheath 408 may be generally cylindrical in shape with a long tubular sheath 320 forming a primary section thereof. At a proximal end, tubular sheath 320 transitions at a sheath shoulder 329 to define a proximal insert 428 of a smaller diameter than the tubular sheath 320 that is sized in both diameter and length to be inserted within and create a fluid-tight connection with the distal end of an alternate embodiment of the ring electrode 403 as further described below. The proximal insert 428 may be formed of alternating sections of recessed wall 416 and protruding wall 418 oriented longitudinally with respect to length of the passive tip sheath 408. The protruding wall section 418 creates tight, friction fit with the ring electrode 403 and the recessed wall sections 416 provide adhesive wells for receiving biocompatible adhesive to permanently connect the passive tip sheath 408 to the ring electrode 403 as further described below.

Toward the distal end, the tubular sheath 420 may transition at a stepped shoulder 421 to a narrower diameter tine recess section 422. Immediately distal to the tine recess section 422 is a tine section 423 from which a plurality of tines 410 protrude at a number of evenly-spaced circumferential locations about the tine section 423. The passive tip sheath 4108 may extend a short length further distally from the tine section 423 in a sloped section 424 that tapers in diameter until terminating at an annular face 425.

The passive tip sheath 408 may define a lumen 426. A relatively long inner coil bore 430 of a constant inner diameter that is sized to extend over the inner conductor coil 120 extends from the proximal insert 428 for a length until the inner conductor coil 120 couples with the tip electrode 105. The inner coil bore 430 transitions to a middle bore 432 of larger inner diameter along a sloped section 431 that gradually increases the inner diameter between the two bore sections. The middle bore 432 is sized in diameter and length to fit about a connection between the connection between the outer insulating tubing 124 and the proximal end of the tip sleeve 109.

The middle bore 432 transitions to a tip sleeve bore 434 of smaller diameter at a squared shoulder 433 that abuts a distal end of the outer insulating tubing 124. The tip sleeve bore 434 covers the remainder of the tip sleeve 109 that forms a crimp connection with the tip electrode 105. The tip sleeve bore 434 then transitions to a tine bore 436, which is generally coextensive with the tine section 423 on the outer surface of the passive tip sheath 408 and which houses the medial shaft section 404 of the tip electrode 105. Finally, the lumen 426 exits the distal end of the passive tip sheath 408 through a tip bore 438 that is of a larger diameter than the tine bore 436 and which is sized to house the barrel section 306 of the tip electrode 105. The annular shelf 437 acts as a shoulder at the change in diameter between the tine bore 436 and the tip bore 438. The annular shelf 437 acts as an axial stop abutting the tip shoulder 309 of the tip electrode 105 to prevent the passive tip sheath 408 from sliding distally off of the lead 100.

FIG. 13 depicts an exemplary steroid capsule 107 that may be placed within the steroid cavity 310 in the barrel section 306 of the tip electrode 105. The steroid capsule 107 may be formed as a cylindrical plug sized to fit snugly within the steroid cavity 320. The steroid capsule 107 may be any of a number of steroids or medicaments prepared in a binder for timed release after implantation of the lead 100 in order to promote healing of any trauma caused by placement of the lead 100 or to deliver a desirable drug for efficacy within the heart. As noted above, the steroid capsule 107 may be adhered within the barrel section 306 with a biocompatible adhesive to ensure that the steroid capsule 107 does not dislodge before completely eluting.

Figure 14A:
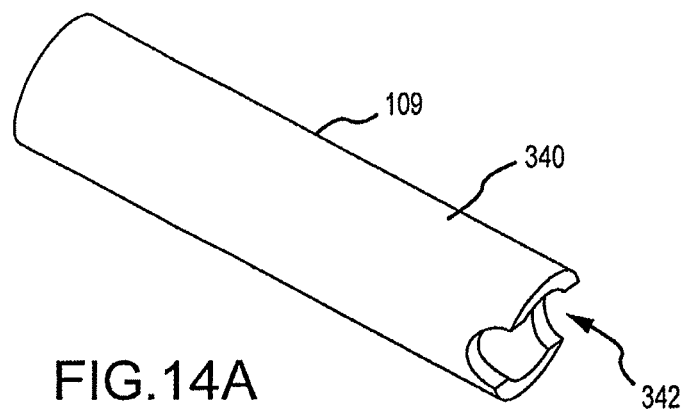
FIGS. 14A and 14B are an isometric view and an isometric cross-sectional view, respectively, of a tip sleeve of the lead of FIGS. 1, 10A, and 10B.
Figure 14B:
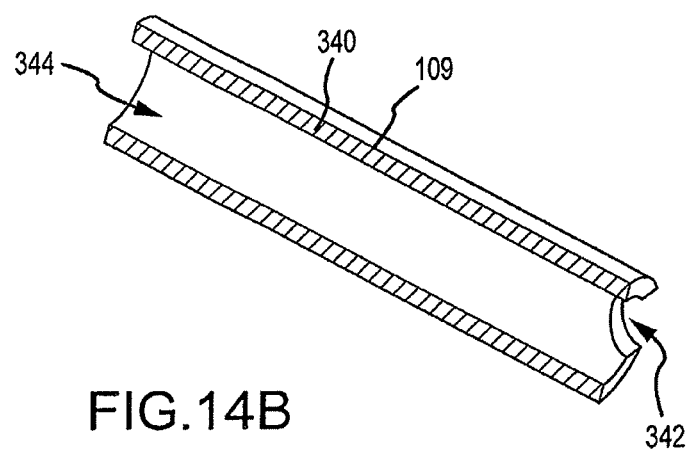

FIGS. 14A and 14B depict an exemplary embodiment of a tip sleeve 109 used to crimp the tip electrode 105 to the inner conductor coil 120. The tip sleeve 109 is formed as a cylindrical sleeve 340 defining a tip sleeve bore 344 of a constant diameter therethrough. The diameter of the tip sleeve bore 344 is selected to be slightly smaller than the outer diameter of the proximal shaft section 302 of the tip electrode 105 plus two times the thickness of the wall of the inner conductor coil 120 in order to provide a crimped connection with the proximal shaft section 302 by sandwiching the inner conductor coil 120 therebetween. One or more semicircular cutouts 342 may be formed in the cylindrical sleeve 340 at the distal end thereof. The cutouts 342 may be provided to allow for visual inspection of the crimp connection between the tip sleeve 109 and the proximal shaft section 302 of the tip electrode 105 during assembly.

The ring electrode 103 is depicted in greater detail in FIGS. 15A and 15B. The ring electrode 103 is generally tubular in shape with various cylindrical sections of varying diameter. A smooth, cylindrical proximal sleeve 350 forms the proximal end of the ring electrode 103 and is sized in length and diameter to fit within the distal end of the outer connecter coil 134 and may be laser welded thereto or otherwise securely mechanically attached to form a permanent mechanical and electrical connection. An adhesive channel 352 is formed distally adjacent the proximal sleeve 350 and is defined by a proximal curb 351 and a distal curb 353. The proximal curb 351 and the distal curb 353 may be of the same diameter, which may be slightly larger in diameter than the proximal sleeve 350. The adhesive channel 352 may be substantially the same diameter as the proximal sleeve 350. The proximal curb 351 may separate the proximal sleeve from the adhesive channel 352. The diameters of the proximal and distal curbs 351, 353 are selected to be substantially the same as the inner diameter of the outer sheath 152 and the surfaces of the proximal and distal curbs 351, 353 are smooth in order to provide a close compression fit with the outer sheath 152. The adhesive channel 352 may define one or more adhesive apertures 354 (two are shown in the exemplary embodiment) in order to introduce a biocompatible adhesive into the channel 352 to bond the ring electrode 103 to the outer sheath 152.

The ring electrode 103 may transition from the adhesive channel 352 via a proximal shoulder 355 adjacent the distal curb 353 to an exposed section 356 of a greater outer diameter. The exposed section 356 may be smooth and cylindrical in shape and is not covered or insulated from the patient's blood or tissue. The exposed section 356 may be made of a precious metal, e.g., PT/Ir or Pt, or another electrically conductive, biocompatible material. The distal end of the exposed section 356 transitions at a distal shoulder 357 to a connection section 360 that may be of a smaller outer diameter than the exposed section 356. The connection section 360 may be formed with a series of flat ribs 358 separated from each other by a series of flat channels 359. The flat ribs 358 may be selected to be of a diameter to increase the bonding surface of the sleeve bore 328 of the passive tip sheath 108 for increased bonding strength and to and create a tight connection therebetween. The flat channels 359 provide areas for a biocompatible adhesive to be introduced and flow to thereby permanently adhere the sleeve bore 328 of the passive tip sheath 108 to the connection section 360 at the distal end of the ring electrode 103.

The ring electrode 103 may also define a lumen of two different bore sizes. A distal bore 362 is sized to be of a slightly larger diameter than the insulating tubing 124 surrounding the inner conductor coil 120 to provide clearance for its passage therethrough. A proximal bore 364 is sized to be substantially the same diameter as the outer diameter of the insulating tubing 124 surrounding the inner conductor coil 120. The insulating tubing 124 and inner conductor coil 120 are thereby able to pass through the proximal bore 364 during assembly. However, the adhesive in the adhesive channel 352 may pass through the adhesive apertures 354 to contact the insulating tubing 124 and thereby adhere the insulating tubing 124 to the ring electrode 103 to act as a strain relief on possible axial pull on the insulating tubing 124 that might act to pull the insulating tubing 124 off of the tip sleeve 109 upon which the distal end of the insulating tubing 124 expands and terminates as further described below. An interior shoulder 366 provides the transition between the smaller diameter proximal bore 364 to the larger diameter distal bore 362.

Figure 27A:
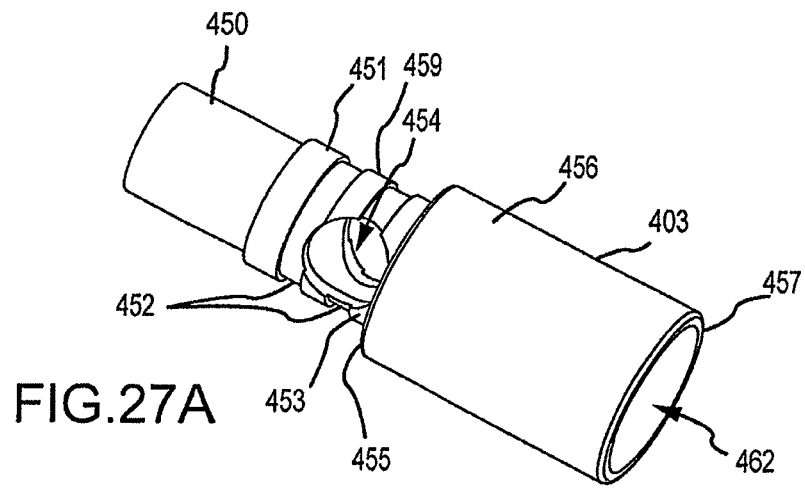
FIGS. 27A and 27B are an isometric view and an isometric cross-sectional view, respectively, of an alternate embodiment of a ring electrode for use in the lead of FIGS. 1, 10A, and 10B.
Figure 27B:
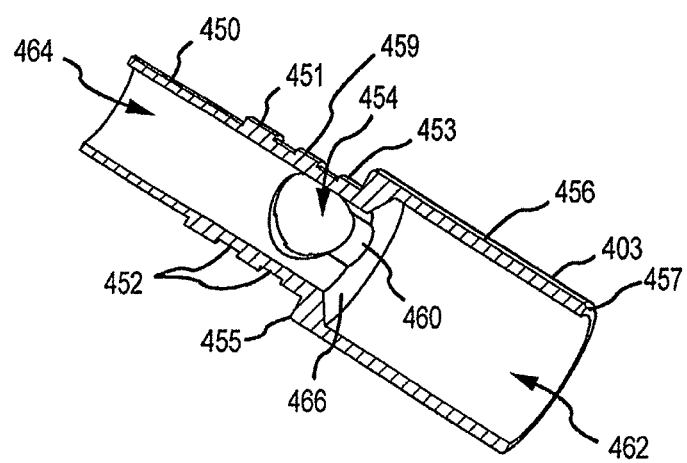
Figure 28A:
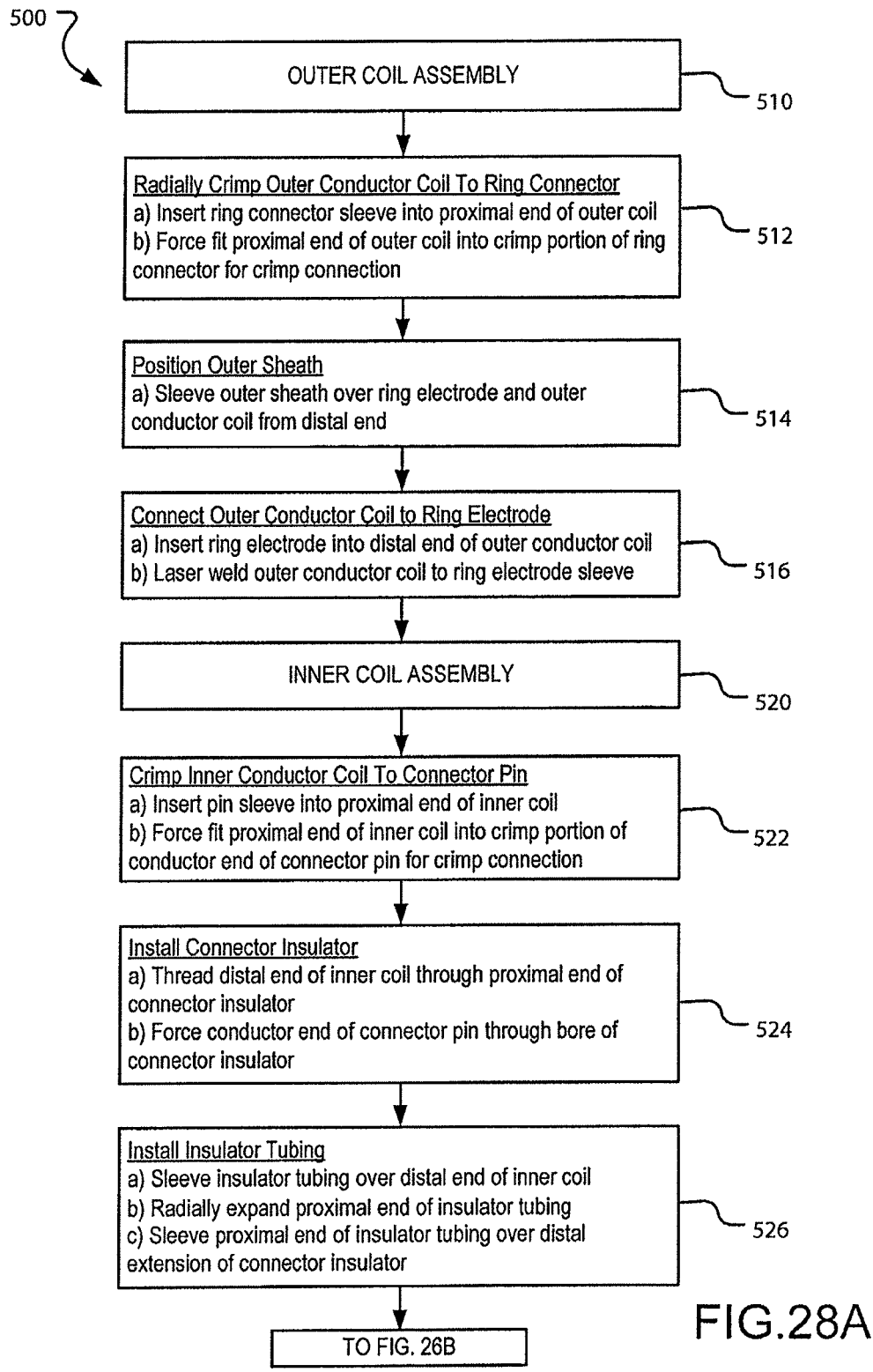
FIGS. 28A and 28B are a flow diagram depicting an exemplary method of assembling an exemplary passive cardiac electrical lead.
Figure 28B:
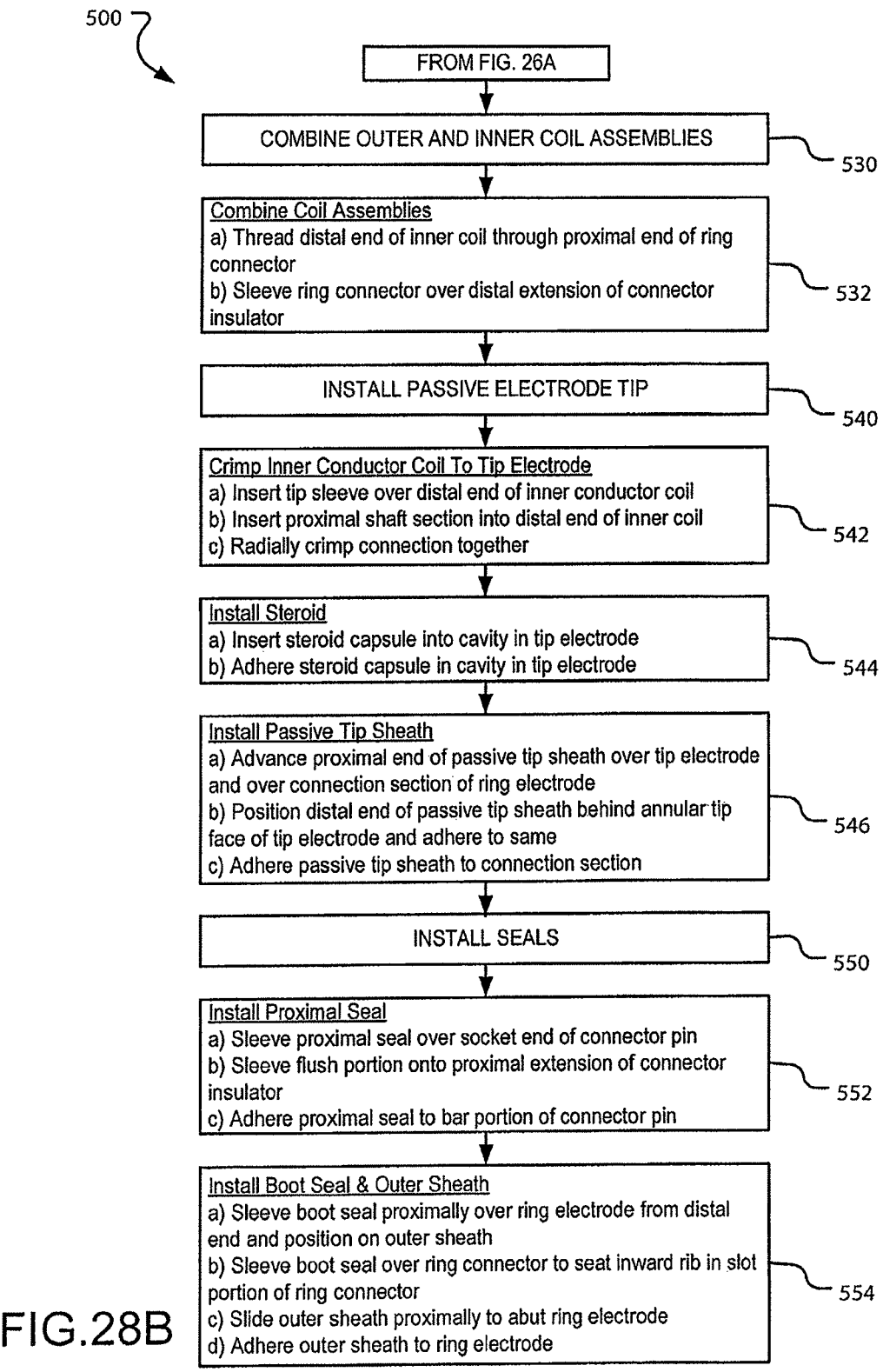

An exemplary alternate embodiment of a ring electrode 403 for use in conjunction with the passive tip sheath 408 of FIGS. 26A and 26B is depicted in greater detail in FIGS. 27A and 27B. The ring electrode 403 is generally tubular in shape with various cylindrical sections of varying diameter. A smooth, cylindrical proximal sleeve 450 forms the proximal end of the ring electrode 403 and is sized in length and diameter to fit within the distal end of the outer connecter coil 134 and may be laser welded thereto or otherwise securely mechanically attached to form a permanent mechanical and electrical connection. Several adhesive channels 452 are formed distally adjacent the proximal sleeve 450 and are defined by a proximal curb 451, a medial curb 459, and a distal curb 453. The proximal, medial, and distal curbs 451, 459, 453 may be of the same diameter, which may be slightly larger in diameter than the proximal sleeve 450. The adhesive channels 452 may be substantially the same diameter as the proximal sleeve 450. The proximal curb 451 may separate the proximal sleeve from the first of the adhesive channels 452. The diameters of the proximal, medial, and distal curbs 451, 459, 453 are selected to be substantially the same as the inner diameter of the outer sheath 152 and the surfaces of the proximal, medial, and distal curbs 451, 459, 453 are smooth in order to provide a close compression fit with the outer sheath 152. One or more adhesive apertures 454 (two are shown in the exemplary embodiment) may be defined in the area of the proximal, medial, and distal curbs 451, 459, 453 and the adhesive channels 452 in order to introduce a biocompatible adhesive into the channels 452 to bond the ring electrode 403 to the outer sheath 152.

The ring electrode 403 may transition to an exposed section 356 of a greater outer diameter from a proximal shoulder 455 adjacent the distal curb 453. The exposed section 456 may be smooth and cylindrical in shape and is not covered or insulated from the patient's blood or tissue. The exposed section 456 may be made of a precious metal, e.g., PT/Ir or Pt, or another electrically conductive, biocompatible material. The distal end of the exposed section 456 may terminate at a distal rim 457 that defines a distal entrance to a lumen of the ring electrode 403. The lumen may be formed with a proximal bore 464 of a smaller diameter than a distal bore 462. An interior shoulder 466 provides the transition between the smaller diameter proximal bore 464 to the larger diameter distal bore 462.

The distal bore 462 may be sized to be of an inner diameter congruent with or slight smaller than the protruding wall section 418 of the passive tip sheath 408 to create a tight, friction fit with the passive tip sheath 408, which is of a larger diameter than the insulating tubing 124 surrounding the inner conductor coil 120 to provide clearance for its passage therethrough. The recessed wall sections 416 of the passive tip sheath 408 provide adhesive wells for receiving biocompatible adhesive to permanently connect the passive tip sheath 408 within the distal bore 462 of the ring electrode 403.

The proximal bore 464 may be sized to be substantially the same diameter as the outer diameter of the insulating tubing 124 surrounding the inner conductor coil 120. The insulating tubing 124 and inner conductor coil 120 are thereby able to pass through the proximal bore 464 during assembly. However, the adhesive in the adhesive channels 452 may pass through the adhesive apertures 454 to contact the insulating tubing 124 and thereby adhere the insulating tubing 124 to the ring electrode 403 to act as a strain relief on possible axial pull on the insulating tubing 124 that might act to pull the insulating tubing 124 off of the tip sleeve 109 upon which the distal end of the insulating tubing 124 expands and terminates as further described below.

Several stages of a method of assembly 500 of a passive cardiac electrical lead are shown in FIGS. 16-25B and a flow chart of the method 500 is shown in FIGS. 26A and 26B. It is to be appreciated that, while FIGS. 26A and 26B reflect an order of assembly and while FIGS. 16-25B are arranged generally consistent with that order by showing consecutive stages for assembling the several parts of the lead 100, several other orders may also be used and the method should not be limited to the order shown.

A first exemplary step of the method 500 may be to assemble the outer coil assembly as indicated in step 510 of FIG. 26A. Assembly of the outer coil may be performed in a series of substeps. As indicated in step 512 of FIG. 26A and shown in FIG. 16, the outer coil 134 may be crimped to the crimp portion 208 of the ring connector 130 to form the outer conductor assembly similar to the crimp connection between the inner coil 120 and the connector pin 112. To form the outer conductor assembly, the ring sleeve 136 may be inserted into the proximal end of the outer coil 134, which is flared radially outward to receive the ring sleeve 136. The ring sleeve 136 may be advanced within the outer coil 134 until the proximal end of the outer coil 134 abuts the proximal flange or flare portion 224 on the ring sleeve 136. The proximal end of the outer coil 134, with the ring sleeve 136 arranged therein, may be forcibly inserted in to the crimp portion 208 of the ring connector 130. As discussed in the description of the parts of the lead 100, the outer diameter of the ring sleeve 136 and the inner diameter of the crimp portion 208 of the ring connector 130 may be adapted to pinch the outer coil 134 against the inner surface of the crimp portion 208 of the ring connector 130. By forcibly inserting the proximal end of the outer coil 134 into the crimp portion 208 of the ring connector 130, the outer coil 134 may be coupled by a friction fit connection to the ring connector 130. The ring connector 130, the outer coil 134, and the ring sleeve 136 may further be mechanically crimped together using a crimping tool to apply a radial crimping force on the crimp portion 208 of the ring connector 130. As the outer coil 134 is forcibly inserted into the crimp portion 208 of the ring connector 130, the proximal flange or flare portion 224 on the ring sleeve 136 may help to keep the ring sleeve 136 at the proximal end of the outer coil 134 and may resist inadvertent advancement of the ring sleeve 136 along or through the outer coil 134.

Once the outer coil 134 is attached to both the ring connector 130 and the ring electrode 103, the outer sheath 152 may be placed on the outer coil assembly as indicated in step 514. The outer sheath 152 may be sleeved over the ring electrode 103 and placed along the outer conductor coil 134 as shown in FIG. 18, where it may easily slide proximally and distally between the ring connector 130 and the ring electrode 103.

A next stage in an exemplary assembly of the lead is described in step 516 of FIG. 26A. In this step, the distal end of the outer coil 134 is sleeved over the proximal sleeve 350 of the ring electrode 103 as shown in FIG. 17. The outer coil 134 may then be laser welded to the proximal sleeve 350. Alternate methods of providing a permanent electrical and mechanical connection between the outer coil 134 and the ring electrode 103 may be used, including, for example, crimping, adhesion with a conductive, biocompatible adhesive, providing a mechanical fastener.

Figure 19:
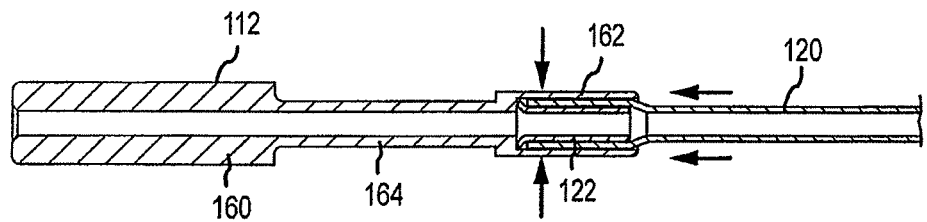
FIG. 19 is a cross-sectional view of a partially assembled lead including the connector pin crimped to the inner coil with a pin sleeve in an exemplary method of assembly of an exemplary passive cardiac electrical lead.

The next primary step in the exemplary method of assembly 500 in FIG. 26A is to assemble the inner coil assembly as indicated in step 520. A first substep in this process may be to crimp the inner conductor coil 120 to the connector pin 112 as indicated in step 522. FIG. 19 shows a stage of the inner coil assembly 520 where the connector pin 112 is coupled to the inner coil 120. The inner coil 120 may be crimped within the conductor end 162 of the connector pin 112 in conjunction with the pin sleeve 122. The pin sleeve 122 may be inserted into the proximal end of the inner coil 120 and may be advanced until the proximal end of the inner coil 120 abuts the proximal flange or flare portion 180 on the pin sleeve 122. The proximal end of the inner coil 120, with the pin sleeve 122 arranged therein, may be forcibly inserted in to the conductor end 162 of the connector pin 112. The connector pin 112 and inner coil 120 are mechanically and electrically coupled through this crimped connection. As discussed in the description of the parts of the lead 100, the outer diameter of the pin sleeve 122 and the inner diameter of the conductor end 162 of the connector pin 112 may be adapted to pinch the inner coil 120 against the inner surface of the conductor end 162 of the connector pin 112. By forcibly inserting the proximal end of the inner coil 120 into the conductor end 162 of the connector pin 112, the inner coil 120 may be coupled by a friction fit and then radially crimped to provide a strong connection to the connector pin 112. As the inner coil 120 is forcibly inserted into the conductor end 162 of the connector pin 112, the proximal flange or flare portion 180 on the pin sleeve 122 may help to keep the pin sleeve 122 at the proximal end of the inner coil 120 and may resist inadvertent advancement of the pin sleeve 122 along or through the inner coil 120.

Figure 20A:
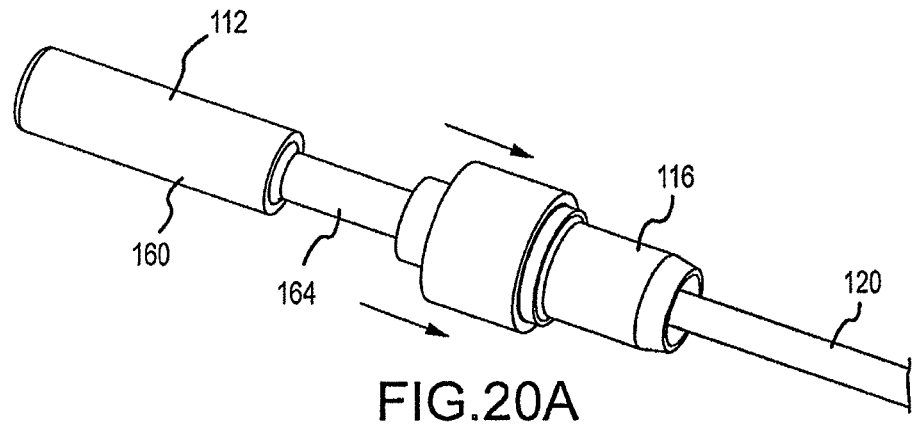
FIG. 20A is an isometric view of the connector insulator placed on the connector pin and the inner coil of the partial assembly of FIG. 19 in an exemplary method of assembly of an exemplary passive cardiac electrical lead.
Figure 20B:
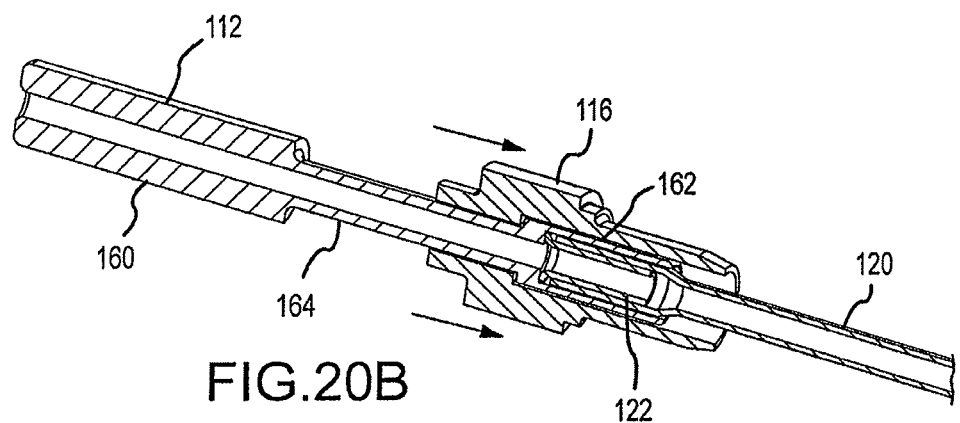
FIG. 20B is a cross-sectional view of FIG. 20A.

Next, as indicated in step 524 of FIG. 26A, the connector insulator 116 may be installed on the connector pin 112. FIGS. 20A and 20B show an isometric view and cross-sectional view, respectively, of this stage of assembly where the connector insulator 116 is positioned on the connector pin 112 and slightly over a portion of the inner conductor coil 120. The distal end of the inner coil 120 may be inserted through the proximal end of the connector insulator 116. As the inner conductor 120 is fully inserted through the connector insulator 116, the conductor end 162 of the connector pin 112 approaches the proximal extension 184 of the connector insulator 116. The outer diameter of the conductor end 162 of the connector pin 112 may be at least slightly larger than the inner diameter of the bore 118. The connector pin 112 may then be forcibly pushed through the bore 118 of the connector insulator 116. As the conductor end 162 of the connector pin 112 passes through the bore 118 of the connector insulator 116, the connector insulator 116 may elastically expand until the conductor end 162 of the connector pin 112 reaches the distal bore 119 beyond bore 118, and the bore 118 may then return to its original shape, thereby locking the connector pin 112 therein. The connector insulator 116 may be freer to move proximally along the connector pin 112 until the proximal seal 114 is placed.

Figure 21A:
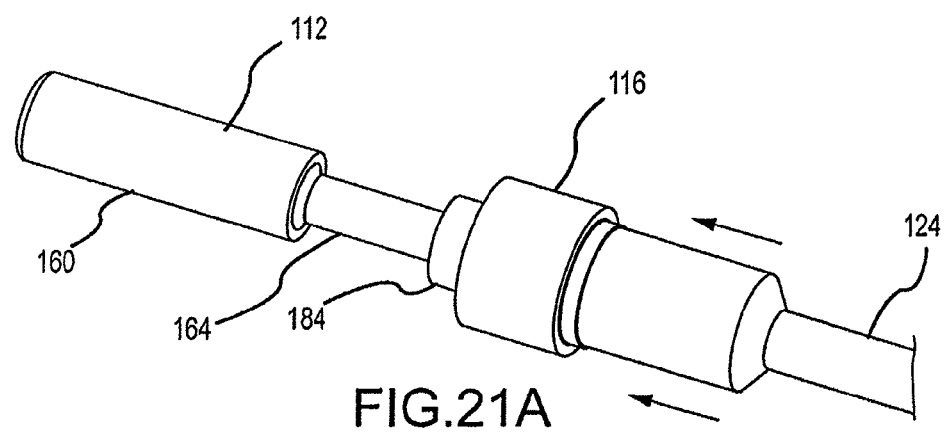
FIG. 21A is an isometric view of the insulator tubing placed over the distal end of the connector insulator and over the inner coil of the partial assembly of FIG. 20A in an exemplary method of assembly of an exemplary passive cardiac electrical lead.
Figure 21B:
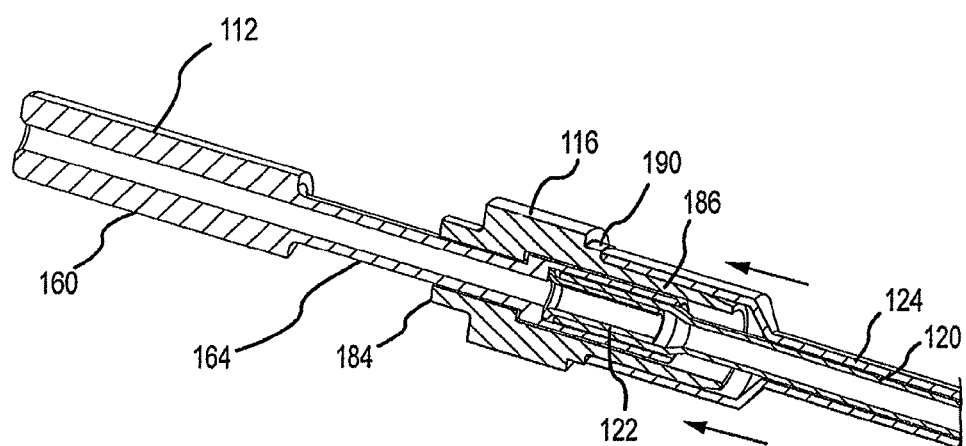
FIG. 21B is a cross-sectional view of FIG. 21A.

The next step in an exemplary inner coil assembly process 520 may be to install or tubing over the inner conductor coil 120 as indicate in step 526 of FIG. 26A. FIGS. 21A and 21B show an isometric view and a cross-sectional view, respectively, of a stage of assembly where the insulator tubing 124 is positioned on the inner conductor coil 120 and the connector insulator 116. The insulator tubing 124 may be sleeved over the distal end of the inner conductor 120. The insulator tubing 124 may be advanced proximally along the inner conductor 120 to cover the inner conductor 120 and the proximal end of the insulator tubing 124 may approach distal extension 186 of the connector insulator 116. The inner diameter of the insulator tubing 124 may be slightly larger than the outer diameter of the inner conductor 120. To sleeve the proximal end of the insulator tubing 124 over the distal extension 186 of the connector insulator 116, the proximal end of the insulator tubing 124 may be dilated by chemical treatment with, heptane, alcohol, or related families of chemicals, for example, and by placement on a mandrel to expand the tubing 124. The treatment of the proximal end of the insulating tubing 124 for expansion may be performed either before or after the insulating tubing 124 is sleeved over the inner conductor coil 120. Once expanded, the proximal end of the tubing 124 may be sleeved over the distal extension 186 of the connector insulator 116 and may be brought into abutting relationship with the inner shoulder 190 of the cascading shoulders. The insulator tubing 124 may thus compress about and frictionally engage the distal extension 186 of the connector insulator 116 securing the insulator tubing 124 against longitudinal and rotational motion relative to the connector insulator 116 and creating a fluid-tight seal.

Figure 22A:
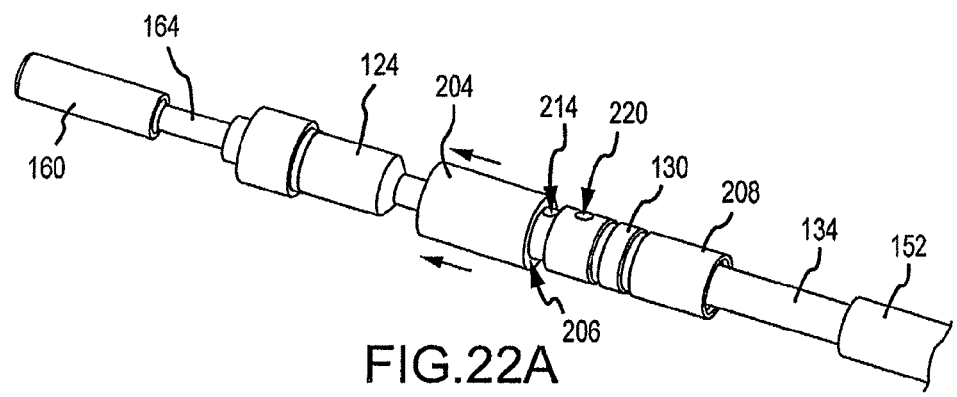
FIG. 22A is an isometric view of the partial assembly of FIG. 18 with the coupled ring connector and outer coil being sleeved over the inner coil toward the connector insulator in an exemplary method of assembly of an exemplary passive cardiac electrical lead.
Figure 22B:
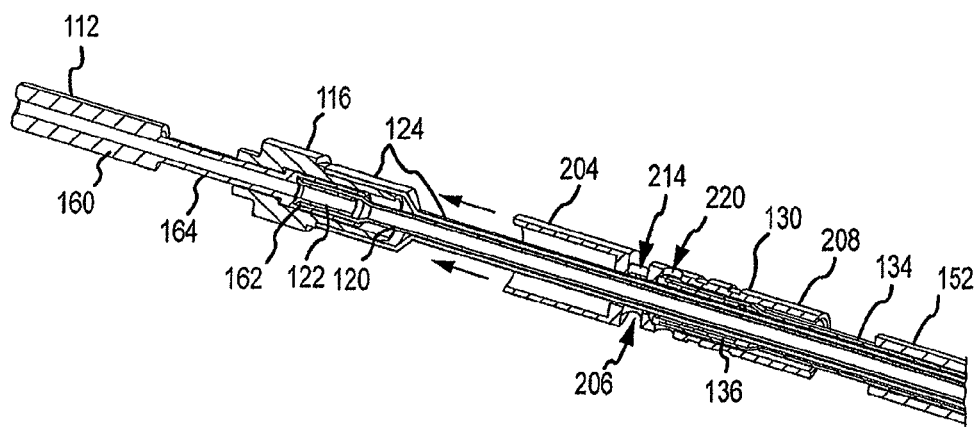
FIG. 22B is a cross-sectional view of FIG. 22A.

A next primary step in the exemplary method of assembly 500 is to combine the outer coil assembly with the inner coil assembly as indicated in step 530 of FIG. 26B. FIGS. 22A and 22B show an isometric view and cross-sectional view, respectively, of a stage of assembly where the outer conductor assembly is sleeved over the inner conductor assembly and insulator tubing 124. At this stage of assembly, as indicated in step 532 of FIG. 26B, the distal end of the inner coil 120 covered by the insulator tubing 124 may be threaded through the proximal end of the ring connector 130 and distally through the outer coil 134 and outer sheath 152. As shown by the arrows in FIGS. 22A and 22B, as the inner conductor 120 and insulator tubing 124 is fully threaded through the ring connector 130, the proximal end of the ring connector 130 may approach the distal extension 186 of the connector insulator 116 that is covered by the insulator tubing 124. The ring connector 130 may be sleeved over the distal extension 186 of the connector insulator 116 and over the insulator tubing 124. The proximal end of the ring connector 130 may approach and abut the outer shoulder 188 of the cascading shoulder of the connector insulator 116. The ring connector 130 may thus frictionally engage the distal extension 186 of the connector insulator 116 through frictionally engaging the outer surface of the insulator tubing 124. This frictional engagement resists relative longitudinal and rotational motion between the outer conductor assembly and the connector insulator 116. It can be seen from FIGS. 22A and 22B that the outer conductor assembly and the inner conductor assembly may be electrically insulated from one another by a combination of the insulator tubing 124 and the connector insulator 116.

Figure 23A:
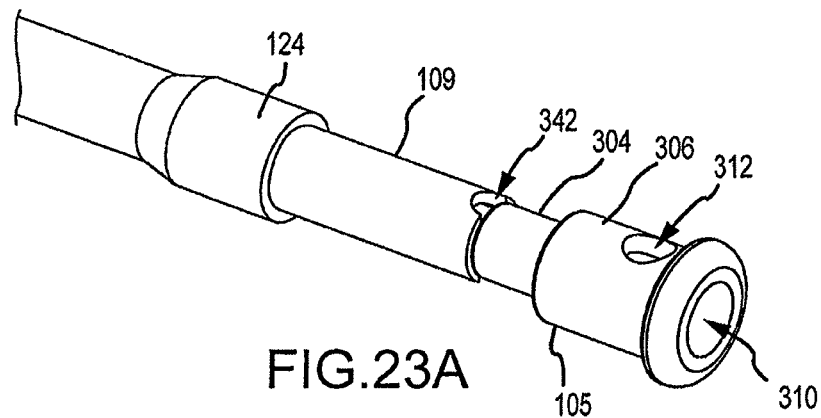
FIG. 23A is an isometric view of the partial assembly of FIG. 22A with the ring connector fully seated on the connector insulator, a proximal seal in place on the connector insulator, and the boot seal being sleeved over the outer sheath toward the ring connector in an exemplary method of assembly of an exemplary passive cardiac electrical lead.
Figure 23B:
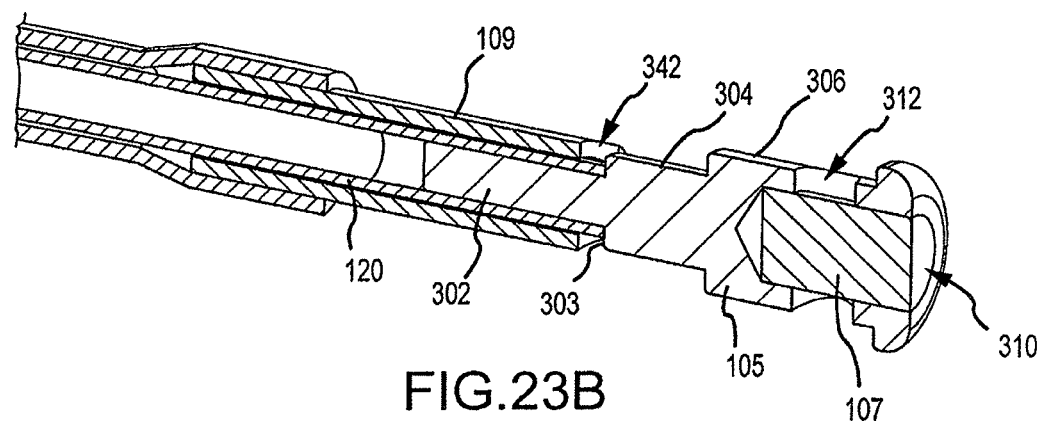
FIG. 23B is a cross-sectional view of FIG. 23A.

In a further primary step in the method 500, the passive electrode tip 106 may be installed on the distal end of the lead 100 as indicated in step 540 of FIG. 26B. In a first operation of this step 540, the inner conductor coil 120 may be connected to the tip electrode 105 as indicated in step 542. FIGS. 23A and 23B show an isometric view and cross-sectional view, respectively, of a stage of assembly where the proximal shaft section 302 of the tip electrode 105 is crimped to the inner conductor coil 120. In order to make this crimped connection, the tip sleeve 109 may first be sleeved over the distal end of the inner conductor coil 120 with the semicircular cutouts 342 directed distally. The proximal shaft section 302 of the tip electrode 105 may then be inserted into the lumen defined within the inner conductor coil 120 and may be advanced until the distal end of the inner coil 120 and the tip sleeve 109 abut the barrel shoulder 305 of the barrel section 306 of the tip electrode 105. The proximal shaft section 302 may be forcibly inserted in to the inner conductor coil 120. The tip electrode 105 and inner conductor coil 120 are mechanically and electrically coupled through this crimped connection. As discussed in the description of the parts of the lead 100, the inner diameter of the tip sleeve 109 and the outer diameter of the proximal shaft section 302 of the tip electrode 105 may be adapted to pinch the inner conductor coil 120 therebetween and create a tight friction fit. The proximal shaft section 302, the tip sleeve 109, and the inner conductor coil 120 may then be radially crimped together to provide a strong connection.

In a next installation operation of the exemplary method 500, a steroid capsule 107 or other medicament may be installed within the tip electrode 105 as indicated in step 544 of FIG. 26B. A steroid capsule 107 or other medicament is depicted installed in the electrode tip 105 in FIG. 23B before the installation of the passive tip sheath 108. This may be one exemplary order, but it is not required as the steroid capsule may be installed at any time from before the tip electrode 105 is connected to the inner conductor coil 120 or to after the passive tip sheath 108 is put in place. The steroid capsule 107 may be inserted into the steroid cavity 310 of the tip electrode 105. Adhesive may be introduced through the glue apertures 312 after the steroid capsule 107 is placed within the cavity 310 to adhere the steroid capsule 107 within the steroid cavity 310. Alternatively, an adhesive may be introduced within the steroid cavity 310 before the steroid capsule 107 is put in place. Excess adhesive may then escape through the glue apertures 312 and operate to adhere the tip bore 338 of the passive tip sheath 108 to the tip electrode 105.

In a further installation operation for the passive electrode tip 105, the passive tip sheath 108 may be installed on the distal end of the lead 100 as indicated in step 546 of FIG. 26B and further shown in FIGS. 24A and 24B. Initially, the passive tip sheath 108 may be advanced proximally over the tip electrode 105 until the sleeve bore 328 within the tubular sheath 320 at the proximal end of the passive tip sheath 108 is positioned over and about the connection section 360 of the ring electrode 103. An adhesive may be applied over the flat ribs 358 and flat channels 359 of the connection section 360 in order to permanently affix the passive tip sheath 108 to the ring electrode 103. The bore sections of the lumen 326 of the passive tip sheath 108 may conform to various diameters of sections of the tip electrode 105, tip sleeve 109, and inner conductor coil 120 housed therein. The distal portion of the passive tip sheath 108 may also be seated against portions of the tip electrode 105 and retained thereby. For example, the annular shelf 337 defining a base of the tip bore 338 of the passive tip sheath 108 may abut the barrel shoulder 305 of the tip electrode 105 to prevent distal movement of the passive tip sheath with respect thereto. Similarly, the annular face 325 may abut the tip shoulder 309 and thereby be retained behind the annular tip face 308.

A final primary step of the exemplary method of assembly 500 is the installation of seals on the lead 100 as indicated in step 550 of FIG. 26B. A first substep may be the installation of the proximal seal 114 as indicated in step 552. FIGS. 25A and 25B show an isometric view and cross-sectional view, respectively, of a stage of assembly where the proximal seal 114 is placed from the proximal end 102 onto the connector insulator 116. At this stage of assembly, the proximal seal 114 may be sleeved over the socket end 160 of the connector pin 112 and onto the proximal extension 184 of the connector insulator 116. As shown in box 552 of FIG. 26, the proximal seal 114 may be stretched to be sleeved over the socket end 160 of the connector pin 112 and advanced to be positioned over the bar portion 164 of the connector pin 112. A flush portion 198 of the proximal seal 114 may be sleeved onto the proximal extension 184 of the connector insulator 116 and the remaining portion may be adhered to the bar portion 164 of the connector pin 112 with a medical adhesive such as silicone adhesive, polyurethane adhesive, epoxy adhesive, or other suitable bio-adaptable adhesive.

In a next step of the exemplary method 500 of assembling a lead 100, the boot seal 140 and the outer sheath 152 may next be placed in their final positions on the lead 100 at this stage of assembly as indicated in step 554 of FIG. 26B. The boot seal 140 may be sleeved over the outer sheath 152 toward the proximal end and the ring connector 130 as shown in FIGS. 25A and 25B while the outer sheath 152 may be sleeved distally to abut the proximal shoulder 355 of the ring electrode 103. In one implementation, the boot seal 140 may be sleeved over the outer sheath 152 before the outer sheath 152 is sleeved over the outer coil 134 as discussed with respect to step 516. Before the outer sheath 152 is finally placed abutting the ring electrode 103, adhesive may be applied to the adhesive channel 352 in the proximal sleeve 350 of the ring electrode 103. The adhesive may pass through the adhesive apertures 354 in the adhesive channel 352 to flow over the insulating tubing 124 within the proximal bore 364 of the ring electrode 103 to adhere the insulating tubing 124 to the ring electrode 103. The outer sheath 152 may then be slid distally over the proximal sleeve 350 of the ring electrode 103 and adhered thereto by the adhesive in the adhesive channel 354.

The boot seal 140 may be further sleeved over the ring connector 130 and the inwardly protruding rib 212 of the boot seal 140 may engage the slot portion 206 of the ring connector 130, thereby longitudinally securing the boot seal 140 relative to the ring connector 130. The narrow diameter, medial bore 146 of the boot seal 140 may also fit snugly around the outer coil 134 between the ring connector 130 and the proximal end of the outer sheath 152, abutting the ends of each when the outer sheath 152 abuts the ring electrode 103 at the distal end 104 of the lead 100. The tapered bore 149 of the tapered portion 148 of the boot seal 140 fits tightly around the outer surface of the outer sheath 152 creating a fluid-tight seal therebetween.

Again, the assembly steps described above are merely one example of a process for assembling a passive medical electrode lead. Other methodologies are possible. For example, in an alternative embodiment, it may be desirable to sleeve the outer sheath 152 and the boot sleeve 140 over the outer coil 134 before the outer coil 134 is affixed to the proximal sleeve of the ring electrode 103. The boot seal 140 may additionally be sleeved over the ring electrode 103 and temporarily placed about the outer sheath 134 until the appropriate step in the process for final placement of the boot seal 140. Because of the final separation distance between the proximal end of the outer sheath 152 and the distal end of the ring connector 130 in the final assembled state, the outer sheath 152 with the boot seal 140 temporarily placed about it can be slid proximally out of the way while the distal end of the outer connecter coil 134 is welded to the ring electrode 103. In this way, the outer sheath 152 and boot seal 140 may be placed on the outer conductor coil 134 without placing strain on the weld join that might occur if the outer sheath 152 and boot seal 140 with smaller internal diameters than the largest outer diameter of the ring electrode 103 were sleeved over the distal end of the ring electrode 103 after it was welded to the outer conductor coil 134.

All directional references (e.g., proximal, distal, upper, lower, upward, downward, left, right, lateral, longitudinal, front, back, top, bottom, above, below, vertical, horizontal, radial, axial, clockwise, and counterclockwise) are only used for identification purposes to aid the reader's understanding of the present invention, and do not create limitations, particularly as to the position, orientation, or use of the invention. Connection references (e.g., attached, coupled, connected, and joined) are to be construed broadly and may include intermediate members between a collection of elements and relative movement between elements unless otherwise indicated. As such, connection references do not necessarily infer that two elements are directly connected and in fixed relation to each other. The exemplary drawings are for purposes of illustration only and the dimensions, positions, order and relative sizes reflected in the drawings attached hereto may vary.

The above specification, examples and data provide a complete description of the structure and use of exemplary embodiments of the invention as defined in the claims. Although various embodiments of the claimed invention have been described above with a certain degree of particularity, or with reference to one or more individual embodiments, those skilled in the art could make numerous alterations to the disclosed embodiments without departing from the spirit or scope of the claimed invention. Other embodiments are therefore contemplated. Many of the implementations described herein are not required and the order of steps or operation may be a matter of choice, dependent on the performance requirements of the particular implementation. Accordingly, the operations making up the embodiments of the technology described herein may be referred to variously as methods, operations, or steps. It should be understood that operations may be performed in any order, unless explicitly claimed otherwise or a specific order is inherently necessitated by the claim language. It is intended that all matter contained in the above description and shown in the accompanying drawings shall be interpreted as illustrative only of particular embodiments and not limiting. Changes in detail or structure may be made without departing from the basic elements of the invention as defined in the following claims.

What is claimed is:

1. A method of assembling a passive medical lead, comprising
    mechanically and electrically coupling an inner conductor coil to a connector pin to form an inner conductor assembly;
    threading the inner conductor assembly through a connector insulator having a distal extension and a proximal extension;
    placing an insulator tubing over the inner conductor coil including sleeving a proximal end of the insulator tubing over the distal extension of the connector insulator to create electrical isolation by a fluid-tight, compression fit therebetween;
    mechanically and electrically coupling an outer conductor coil to a ring connector to form an outer conductor assembly;
    threading the inner conductor assembly through the outer conductor assembly and sleeving the ring connector on the distal extension of the connector insulator and over the insulator tubing; and
    sleeving a proximal seal over a socket end of the connector pin, including seating a flush portion of the proximal seal on the proximal extension of the connector insulator and seating a seal portion of the proximal seal on a bar portion of the connector pin between the socket end of the connector pin and the proximal extension of the connector insulator.

2. The method of claim 1 further comprising adhering the sealing portion of the proximal seal to the bar portion of the connector pin.

3. The method of claim 1, wherein the operation of mechanically and electrically coupling an inner conductor coil to a connector pin further comprises
    inserting a pin sleeve into a proximal end of the inner conductor coil; and
    forcibly inserting the proximal end of the inner conductor coil into a conductor end of the connector pin.

4. The method of claim 1, wherein the operation of threading the inner conductor assembly through a connector insulator further comprises forcibly threading a portion of the connector pin, through a bore in the connector insulator.

5. The method of claim 1, wherein the operation of placing the insulator tubing over the inner conductor coil comprises threading the inner coil through the insulator tubing.

6. The method of claim 1, wherein the operation of sleeving a proximal end of the insulator tubing over the distal extension of the connector insulator further comprises chemically treating and dilating the proximal end of the insulator tubing.

7. The method of claim 1, wherein the operation of sleeving a proximal end of the insulator tubing over the distal extension of the connector insulator further comprises abutting a proximal end of the insulator tubing against an inner shoulder on the connector insulator.

8. The method of claim 1, wherein the operation of mechanically and electrically coupling an outer conductor coil to a ring connector further comprises
    inserting a ring sleeve into a proximal end of the outer conductor coil; and forcibly inserting the proximal end of the outer conductor coil into a crimp portion of the ring connector.

9. The method of claim 1, wherein the operation of sleevably arranging the ring connector on the distal extension of the connector insulator further comprises sleeving the ring connector over the proximal end of the insulator tubing and the distal extension of the connector insulator and abutting a proximal end of the ring connector against an outer shoulder of the connector insulator.

10. The method of claim 1, further comprising
sleeving a boot seal over the distal end of the outer conductor assembly to bring the boot seal up to the ring connector;
sleeving the boot seal over the ring connector; and
seating an inwardly protruding rib of the boot seal into a slot portion of the ring connector.

11. The method of claim 1 further comprising mechanically and electrically coupling a distal end of the outer conductor coil to a ring electrode to further form the outer conductor assembly.

12. The method of claim 1 further comprising mechanically and electrically coupling a distal end of the inner conductor coil to a tip electrode after threading the inner conductor assembly through the outer conductor assembly.

13. The method of claim 1 further comprising sleeving an outer sheath over the outer conductor coil to further form the outer conductor assembly.

14. A method of assembling a passive medical lead, comprising
assembling an inner conductor assembly including a flexible inner conductor of a first diameter and an insulating covering over the flexible inner conductor;
assembling an outer conductor assembly including a tubular flexible outer conductor of a second diameter larger than the first diameter and a thickness of the insulating covering; and
threading the inner conductor assembly through the outer conductor assembly.

15. The method of claim 14 further comprising mechanically and electrically coupling the flexible inner conductor to a connector pin.

16. The method of claim 14 further comprising threading the inner conductor assembly through a connector insulator having a distal extension and a proximal extension.

17. The method of claim 16 further comprising
sleeving a proximal end of the insulating covering over the distal extension of the connector insulator to create electrical isolation by a fluid-tight, compression fit therebetween.

18. The method of claim 16 further comprising
mechanically and electrically coupling the flexible inner conductor to a connector pin; and
sleeving a proximal seal over a socket end of the connector pin, including seating a flush portion of the proximal seal on the proximal extension of the connector insulator and seating a seal portion of the proximal seal on a bar portion of the connector pin between the socket end of the connector pin and the proximal extension of the connector insulator.

19. The method of claim 14 further comprising mechanically and electrically coupling the flexible outer conductor to a ring connector.

20. The method of claim 19, wherein
the passive medical lead further comprises a connector insulator having a distal extension; and wherein
the method further comprises sleeving the ring connector on the distal extension of the connector insulator and over the insulating covering to create a fluid-tight, friction fit therebetween.

* * * * *